United States Patent
Olde et al.

(10) Patent No.: US 8,715,216 B2
(45) Date of Patent: May 6, 2014

(54) METHOD AND DEVICE FOR PROCESSING A TIME-DEPENDENT MEASUREMENT SIGNAL

(75) Inventors: Bo Olde, Lund (SE); Kristian Solem, Kävlinge (SE)

(73) Assignee: Gambro Lundia AB, Lund (SE)

( * ) Notice: Subject to any disclaimer, the term of this patent is extended or adjusted under 35 U.S.C. 154(b) by 558 days.

(21) Appl. No.: 13/000,856

(22) PCT Filed: Jun. 26, 2009

(86) PCT No.: PCT/EP2009/004641
§ 371 (c)(1),
(2), (4) Date: Dec. 22, 2010

(87) PCT Pub. No.: WO2009/156175
PCT Pub. Date: Dec. 30, 2009

(65) Prior Publication Data
US 2011/0112595 A1    May 12, 2011

Related U.S. Application Data

(60) Provisional application No. 61/075,774, filed on Jun. 26, 2008.

(30) Foreign Application Priority Data

Jun. 26, 2008   (SE) ...................................... 0801517

(51) Int. Cl.
*A61M 37/00*   (2006.01)
(52) U.S. Cl.
USPC ...................................................... 604/6.11

(58) Field of Classification Search
USPC ...................... 604/4.01, 5.01, 6.09, 6.1, 6.11
See application file for complete search history.

(56) References Cited

U.S. PATENT DOCUMENTS

| | | | |
|---|---|---|---|
| 6,077,443 | A | 6/2000 | Goldau |
| 6,623,443 | B1 | 9/2003 | Polaschegg |
| 2005/0010118 | A1 | 1/2005 | Toyoda et al. |

FOREIGN PATENT DOCUMENTS

| | | |
|---|---|---|
| EP | 0 248 633 B1 | 12/1987 |
| EP | 0 328 163 A2 | 8/1989 |
| JP | 11-513270 | 11/1999 |
| JP | 2005-233681 | 9/2005 |
| WO | WO 97/10013 | 3/1997 |
| WO | WO 98/20918 | 5/1998 |

*Primary Examiner* — Leslie Deak
(74) *Attorney, Agent, or Firm* — Finnegan, Henderson, Farabow, Garrett & Dunner LLP

(57) ABSTRACT

A monitoring device is arranged to receive a time-dependent measurement signal from a pressure sensor in a fluid containing system, which is associated with a first pulse generator and a second pulse generator. The pressure sensor is arranged in the fluid containing system to detect a first pulse originating from the first pulse generator and a second pulse originating from the second pulse generator. The monitoring device is configured to process the measurement signal to remove the first pulse. In this process, the monitoring device receives the measurement signal, obtains a first pulse profile which is a predicted temporal signal profile of the first pulse, and filters the measurement signal in the time-domain, using the first pulse profile, to essentially eliminate the first pulse while retaining the second pulse. The fluid containing system may include an extracorporeal blood flow circuit and a blood circuit of a human patient.

23 Claims, 10 Drawing Sheets

METHOD AND DEVICE FOR PROCESSING A TIME-DEPENDENT MEASUREMENT SIGNAL

This application is a national phase application based on PCT/EP2009/004641 filed Jun. 26, 2009, which claims the benefit of Swedish Patent Application No. SE 0801517-4, filed Jun. 26, 2008, and U.S. Provisional Application No. 61/075,774, filed Jun. 26, 2008, the contents of all of which are incorporated herein by reference.

TECHNICAL FIELD

The present invention generally relates to processing of time-dependent measurement signals obtained from a fluid containing system, and in particular to filtering such a measurement signal for removal of pressure pulses originating from a specific pulse generator. The present invention is e.g. applicable in fluid containing systems for extracorporeal blood treatment.

BACKGROUND ART

In extracorporeal blood treatment, blood is taken out of a patient, treated and then reintroduced into the patient by means of an extracorporeal blood flow circuit. Generally, the blood is circulated through the circuit by one or more pumping devices. The circuit is connected to a blood vessel access of the patient, typically via one or more access devices, such as needles or catheters, which are inserted into the blood vessel access. Such extracorporeal blood treatments include hemodialysis, hemodiafiltration, hemofiltration, plasmapheresis, etc.

US2005/0010118 proposes a technique for monitoring a patient's pulse rate, blood pressure and also the condition of the blood vessel access, by identifying a frequency component of the pressure wave caused by the patent's heartbeat among other pressure waves in the extracorporeal blood flow circuit, by operating a frequency analysis, such as a Fourier transformation, on a pressure signal obtained from a pressure sensor in the extracorporeal blood flow circuit. As noted in US2005/0010118, it might be difficult to extract the relevant frequency component from a mixture of frequency components caused by mechanical devices in the extracorporeal blood flow circuit and by the heartbeat. In particular, the frequency component of the heartbeat may overlap with a frequency component of the mechanical devices. To overcome this limitation, US2005/0010118 proposes e.g. changing the frequency of the blood pump within a certain range of a basic operating frequency during the treatment procedure. The pressure signal from the pressure sensor in the extracorporeal blood flow circuit is analysed by FFT (Fast Fourier Transform), which is not suited for detection of frequency components whose frequencies are constantly changing. The FFT analysis is alleged to reduce the frequency components caused by the blood pump. However, periodic events caused by other mechanical devices in the extracorporeal blood flow circuit, such as valves, may still interfere with the monitoring. Further, it may be undesirable to operate the blood pump with a constantly changing pumping frequency during the treatment procedure. For example, if the extracorporeal blood flow circuit is part of a dialysis machine, the dialysis dose will decline with changed pumping frequency even at unchanged average flow through the extracorporeal blood flow circuit.

Thus, there is a need for an alternative technique for identifying the patent's heartbeat among other pressure waves in a fluid, and in particular a technique with an improved ability to handle the situation when the frequency of the patient's heartbeat is relatively weak and/or at least partially coincides with a frequency component of these other pressure waves and/or is changing over time.

Corresponding needs may arise in other fields of technology. Thus, generally speaking, there is a need for an improved technique for processing a time-dependent measurement signal obtained from a pressure sensor in a fluid containing system associated with a first pulse generator and a second pulse generator, in order to monitor a functional parameter of the fluid containing system by isolating a signal component originating from the second pulse generator among signal components originating from the first and second pulse generator.

SUMMARY

It is an object of the invention to at least partly fulfil one or more of the above-identified needs in view of the prior art.

This and other objects, which will appear from the description below, are at least partly achieved by means of a method, a control device, and a computer program product according to the independent claims, embodiments thereof being defined by the dependent claims.

A first aspect of the invention is a method for processing a time-dependent measurement signal obtained from a pressure sensor in a fluid containing system associated with a first pulse generator and a second pulse generator, wherein the pressure sensor is arranged in the fluid containing system to detect a first pulse originating from the first pulse generator and a second pulse originating from the second pulse generator, said method comprising: receiving the measurement signal; obtaining a first pulse profile which is a predicted temporal signal profile of the first pulse; and filtering the measurement signal in the time-domain, using the first pulse profile, to essentially eliminate the first pulse while retaining the second pulse.

In one embodiment, the step of filtering comprises subtracting the first pulse profile from the measurement signal, wherein the step of subtracting may comprise adjusting a phase of the first pulse profile in relation to the measurement signal, wherein said phase may be indicated by phase information obtained from a phase sensor coupled to the first pulse generator, or from a control unit for the first pulse generator.

In one embodiment, the first pulse profile is obtained in a reference measurement in said fluid containing system, wherein the reference measurement comprises the steps of: operating the first pulse generator to generate at least one first pulse, and obtaining the first pulse profile from a reference signal generated by a reference pressure sensor in the fluid containing system. The first pulse generator may be operated to generate a sequence of first pulses during the reference measurement, and the first pulse profile may be obtained by identifying and averaging a set of first pulse segments in the reference signal. Alternatively or additionally, the reference measurement may be effected intermittently during operation of the fluid containing system to provide an updated first pulse profile. Alternatively or additionally, the pressure sensor may be used as said reference pressure sensor. Alternatively or additionally, the fluid containing system may be operated, during the reference measurement, such that the reference signal contains a first pulse and no second pulse. Alternatively, the reference measurement comprises: obtaining a combined pulse profile based on a first reference signal containing a first pulse and a second pulse; obtaining a second pulse profile based on a second reference signal containing a second pulse and no first pulse, and obtaining the predicted signal profile by subtracting the second pulse profile from the combined pulse profile.

In one embodiment, the step of obtaining comprises obtaining a predetermined signal profile, wherein the step of obtaining may further comprise modifying the predetermined signal profile according to a mathematical model based on a current value of one or more system parameters of the fluid containing system.

In one embodiment, the method further comprises the step of obtaining a current value of one or more system parameters of the fluid containing system, wherein the first pulse profile is obtained as a function of the current value.

In one embodiment, the step of obtaining the first pulse profile comprises: identifying, based on the current value, one or more reference profiles in a reference database; and obtaining the first pulse profile based on said one or more reference profiles. The system parameter(s) may be indicative of the rate of first pulses in the fluid containing system. The first pulse generator may comprise a pumping device and the system parameter may be indicative of a pump frequency of the pumping device. Each reference profile in the reference database may be obtained by a reference measurement in the fluid containing system for a respective value of said one or more system parameters.

In one embodiment, the step of obtaining the first pulse profile comprises: identifying, based on the current value, one or more combinations of energy and phase angle data in a reference database; and obtaining the first pulse profile based on said one or more combinations of energy and phase angle data. The first pulse profile may be obtained by combining a set of sinusoids of different frequencies, wherein the amplitude and phase angle of each sinousoid may be given by said one or more combinations of energy and phase angle data.

In one embodiment, the step of obtaining the first pulse profile comprises: inputting the current value into an algorithm which calculates the response of the pressure sensor based on a mathematical model of the fluid containing system.

In one embodiment, the step of filtering comprises subtracting the first pulse profile from the measurement signal, and the step of subtracting is preceded by an adjustment step, in which at least one of the amplitude, the time scale and the phase of the first pulse profile is adjusted with respect to the measurement signal. The adjustment step may comprise minimizing a difference between the first pulse profile and the measurement signal.

In one embodiment, the step of filtering comprises: supplying the first pulse profile as input to an adaptive filter; calculating an error signal between the measurement signal and an output signal of the adaptive filter; and providing the error signal as input to the adaptive filter, whereby the adaptive filter is arranged to essentially eliminate the first pulse in the error signal. The adaptive filter may comprise a finite impulse response filter with filter coefficients that operate on the first pulse profile to generate the output signal, and an adaptive algorithm which optimizes the filter coefficients as a function of the error signal and the first pulse profile. Alternatively or additionally, the method may further comprise the step of controlling the adaptive filter to lock the filter coefficients, based on a comparison of the rate and/or amplitude of the second pulses to a limit value.

In one embodiment, the fluid containing system comprises an extracorporeal blood flow circuit for connection to a blood system in a human body, and wherein the first pulse generator comprises a pumping device in the extracorporeal blood flow circuit, and wherein the second pulse generator comprises a physiological pulse generator in the human body. The second pulse generator may be at least one of a heart, a breathing system, and a vasomotor affected by an autonomic nervous system. In one implementation, the extracorporeal blood flow circuit comprises an arterial access device, a blood processing device, and a venous access device, wherein the human blood system comprises a blood vessel access, wherein the arterial access device is configured to be connected to the human blood system, wherein the venous access device is configured to be connected to the blood vessel access to form a fluid connection, and wherein the first pulse generator comprises a pumping device arranged in the extracorporeal blood flow circuit to pump blood from the arterial access device through the blood processing device to the venous access device, said method comprising the step of receiving the measurement signal either from a venous pressure sensor located downstream of the pumping device, or from an arterial pressure sensor located upstream of the pumping device.

A second aspect of the invention is a computer program product comprising instructions for causing a computer to perform the method according to the first aspect.

A third aspect of the invention is a device for processing a time-dependent measurement signal obtained from a pressure sensor in a fluid containing system associated with a first pulse generator and a second pulse generator, wherein the pressure sensor is arranged in the fluid containing system to detect a first pulse originating from the first pulse generator and a second pulse originating from the second pulse generator, said device comprising: an input for the measurement signal; a signal processor connected to said input and comprising a processing module configured to obtain a first pulse profile which is a predicted temporal signal profile of the first pulse, and to filter the measurement signal in the time-domain, using the first pulse profile, to essentially eliminate the first pulse while retaining the second pulse.

A fourth aspect of the invention is a device for processing a time-dependent measurement signal obtained from a pressure sensor in a fluid containing system associated with a first pulse generator and a second pulse generator, wherein the pressure sensor is arranged in the fluid containing system to detect a first pulse originating from the first pulse generator and a second pulse originating from the second pulse generator, said device comprising: means for receiving the measurement signal; means for obtaining a first pulse profile which is a predicted temporal signal profile of the first pulse; and means for filtering the measurement signal in the time-domain, using the first pulse profile, to essentially eliminate the first pulse while retaining the second pulse.

A fifth aspect is a method for processing a time-dependent measurement signal obtained from a pressure sensor in a fluid containing system associated with a first pulse generator and a second pulse generator, wherein the pressure sensor is arranged in the fluid containing system to detect a first pulse originating from the first pulse generator and a second pulse originating from the second pulse generator, said method comprising: receiving the measurement signal; obtaining a standard signal profile of the first pulse; and subtracting the standard signal profile from the measurement signal in the time-domain, wherein the standard signal profile has such an amplitude and phase that the first pulse is essentially eliminated and the second pulse is retained.

A sixth aspect is a device for processing a time-dependent measurement signal obtained from a pressure sensor in a fluid containing system associated with a first pulse generator and a second pulse generator, wherein the pressure sensor is arranged in the fluid containing system to detect a first pulse originating from the first pulse generator and a second pulse originating from the second pulse generator, said device comprising: an input for the measurement signal; a signal processor connected to said input and comprising a processing module configured to obtain a standard signal profile of the first pulse, and to subtract the standard signal profile from the measurement signal in the time-domain, wherein the standard signal profile has such an amplitude and phase that the first pulse is essentially eliminated and the second pulse is retained.

Embodiments of the third to sixth aspects may correspond to the above-identified embodiments of the first aspect.

Still other objectives, features, aspects and advantages of the present invention will appear from the following detailed description, from the attached claims as well as from the drawings.

BRIEF DESCRIPTION OF THE DRAWINGS

Exemplifying embodiments of the invention will now be described in more detail with reference to the accompanying schematic drawings.

DETAILED DESCRIPTION OF EXEMPLIFYING EMBODIMENTS

In the following, exemplifying embodiments of the invention will be described with reference to fluid containing systems in general. Thereafter, the embodiments and implementations of the invention will be further exemplified in the context of systems for extracorporeal blood treatment.

Throughout the following description, like elements are designated by the same reference signs.

General

Figure 1:
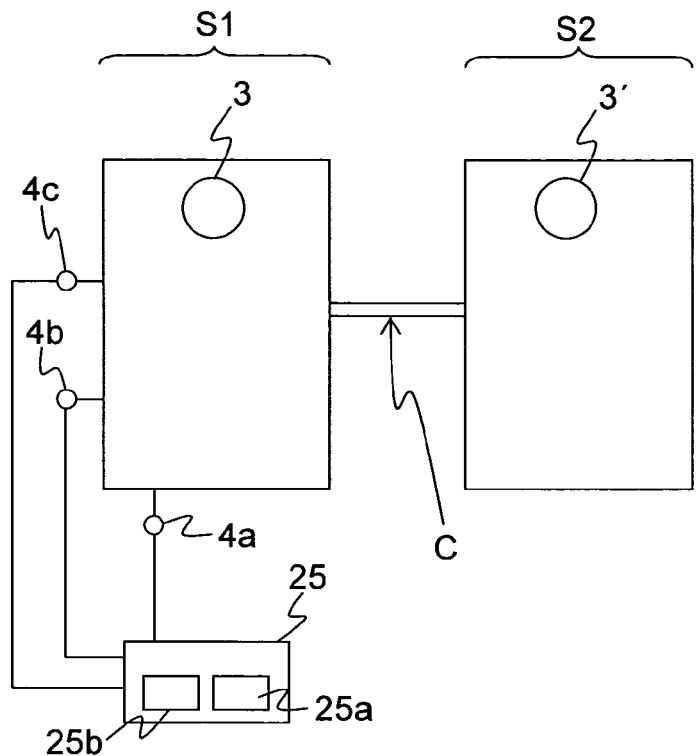
FIG. 1 is a schematic view of a general fluid containing system in which the inventive data processing may be used for filtering a pressure signal.

FIG. 1 illustrates a fluid containing system in which a fluid connection C is established between a first fluid containing sub-system S1 and a second fluid containing sub-system S2. The fluid connection C may or may not transfer fluid from one sub-system to the other. A first pulse generator 3 is arranged to generate a series of pressure waves in the fluid within the first sub-system S1, and a second pulse generator 3' is arranged to generate a series of pressure waves in the fluid within the second sub-system S2. A pressure sensor 4a is arranged to measure the fluid pressure in the first sub-system S1. Pressure waves generated by the second pulse generator 3' will travel from the second sub-system S2 to the first sub-system S1, via the connection C, and thus second pulses originating from the second pulse generator 3' will be detected by the pressure sensor 4a in addition to first pulses originating from the first pulse generator 3. It is to be noted that either one of the first and second pulse generators 3, 3' may include more than one pulse-generating device. Further, any such pulse-generating device may or may not be part of the respective sub-system S1, S2.

The system of FIG. 1 further includes a surveillance device 25 which is connected to the pressure sensor 4a, and possibly to one or more additional pressure sensors 4b, 4c, as indicated in FIG. 1. Thereby, the surveillance device 25 acquires one or more pressure signals that are time-dependent to provide a real time representation of the fluid pressure in the first sub-system S1.

Generally, the surveillance device 25 is configured to monitor a functional state or functional parameter of the fluid containing system, by isolating and analysing one or more second pulses in one of the pressure signals. As will be further exemplified in the following, the functional state or parameter may be monitored to identify a fault condition, e.g. in the first or second sub-systems S1, S2, the second pulse generator 3' or the fluid connection C. Upon identification of a fault condition, the surveillance device 25 may issue an alarm or warning signal and/or alert a control system of the first or second sub-systems S1, S2 to take appropriate action. Alternatively or additionally, the surveillance device 25 may be configured to record or output a time sequence of values of the functional state or parameter.

Depending on implementation, the surveillance device 25 may use digital components or analog components, or a combination thereof, for receiving and processing the pressure signal. The device 25 may thus be a computer, or a similar data processing device, with adequate hardware for acquiring and processing the pressure signal in accordance with different embodiments of the invention. Embodiments of the invention may e.g. be implemented by software instructions that are supplied on a computer-readable medium for execution by a processor 25a in conjunction with a memory unit 25b in the computer.

Typically, the surveillance device 25 is configured to continuously process the time-dependent pressure signal(s) to isolate any second pulses. This processing is schematically depicted in the flow chart of FIG. 2. The illustrated processing involves a step 201 of obtaining a first pulse profile u(n) which is a predicted temporal signal profile of the first pulse(s), and a step 202 of filtering the pressure signal d(n), or a pre-processed version thereof, in the time-domain, using the first pulse profile u(n), to essentially eliminate or cancel the first pulse(s) while retaining the second pulse(s) contained in d(n).

In the context of the present disclosure, n indicates a sample number and is thus equivalent to a (relative) time point in a time-dependent signal. In step 203, the resulting filtered signal e(n) is then analysed for the purpose of monitoring the aforesaid functional state or parameter.

The first pulse profile is a shape template or standard signal profile, typically given as a time-sequence of data values, which reflects the shape of the first pulse in the time domain. The first pulse profile is also denoted "predicted signal profile" in the following description.

By "essentially eliminating" is meant that the first pulse(s) is(are) removed from the pressure signal to such an extent that the second pulse(s) can be detected and analysed for the purpose of monitoring the aforesaid functional state or parameter.

By filtering the pressure signal in the time-domain, using the first pulse profile, it is possible to essentially eliminate the first pulses and still retain the second pulses, even if the first and second pulses overlap or nearly overlap in the frequency domain. Such a frequency overlap is not unlikely, e.g. if one or both of the first and second pulses is made up of a combination of frequencies or frequency ranges.

Furthermore, the frequency, amplitude and phase content of the first pulse or the second pulse may vary over time. Such variations may be the result of an active control of the first and/or second pulse generator 3, 3', or be caused by drifts in the first and/or second pulse generator 3, 3' or by changes in the hydrodynamic properties of the sub-systems S1, S2 or the fluid connection C. Frequency variations may occur, e.g., when the second pulse generator 3' is a human heart, and the second sub-system S2 thus is the blood system of a human. In healthy subjects under calm conditions, variations in heart rhythm (heart rate variability, HRV) may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

Any frequency overlap may make it impossible or at least difficult to isolate the second pulses in the pressure signal by conventional filtering in the frequency domain, e.g. by operating a comb filter and/or a combination of band-stop or notch filters, typically cascade coupled, on the pressure signal to block out all frequency components originating from the first pulse generator 3. Furthermore, frequency variations make it even harder to successfully isolate second pulses in the pressure signal, since the frequency overlap may vary over time. Even in the absence of any frequency overlap, frequency variations make it difficult to define filters in the frequency domain.

Depending on how well the first pulse profile represents the first pulse(s) in the pressure signal, it may be possible to isolate the second pulses by means of the inventive filtering in the time-domain even if the first and second pulses overlap in frequency, and even if the second pulses are much smaller in amplitude than the first pulses.

Still further, the inventive filtering in the time domain may allow for a faster isolation of second pulses in the pressure signal than a filtering process in the frequency domain. The former may have the ability to isolate a single second pulse in the pressure signal whereas the latter may need to operate on a sequence of first and second pulses in the pressure signal. Thus, the inventive filtering may enable faster determination of the functional state or functional parameter of the fluid containing system.

Figure 3:
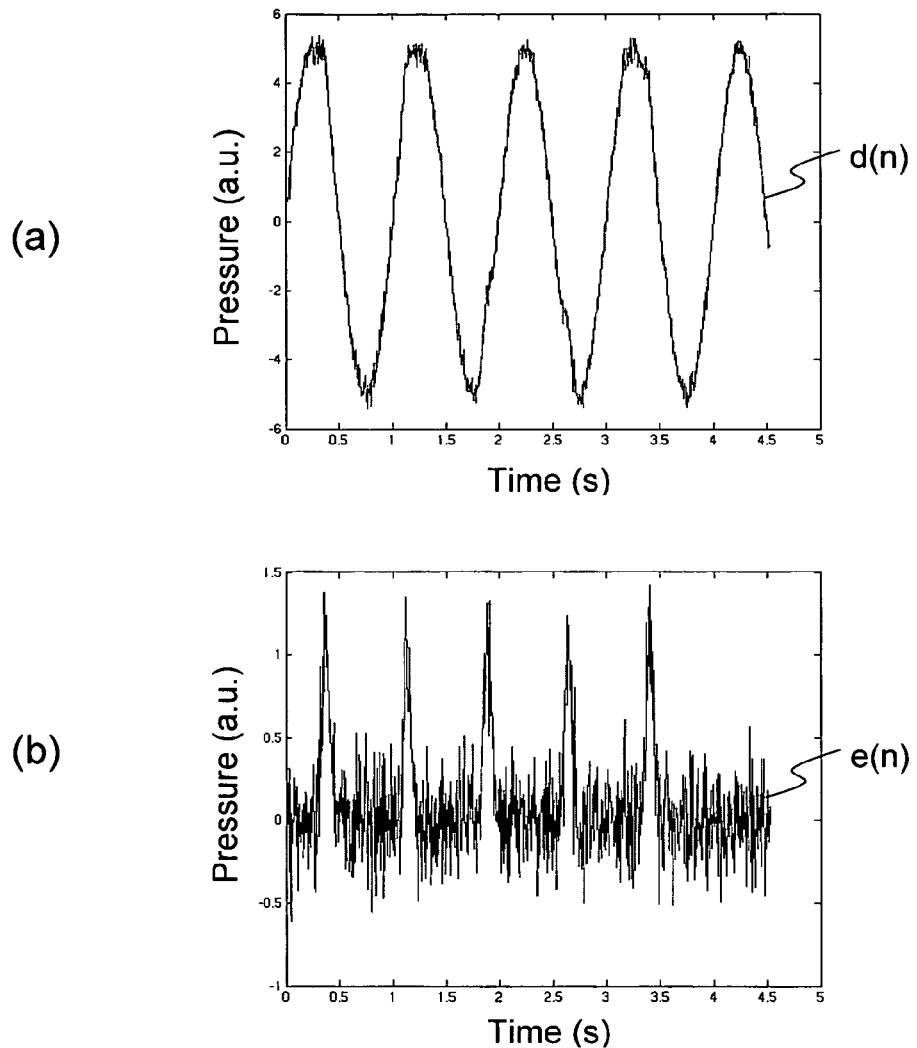
FIG. 3(a) is a plot of a pressure signal as a function of time.
FIG. 3(b) is a plot of the pressure signal after filtering.

The effectiveness of the inventive filtering is exemplified in FIG. 3, in which FIG. 3(*a*) shows an example of a time-dependent pressure signal d(n) containing first and second pulses with a relative magnitude of 10:1. The first and second pulses have a frequency of 1 Hz and 1.33 Hz, respectively. Due to the difference in magnitude, the pressure signal is dominated by the first pulses. FIG. 3(*b*) shows the time-dependent filtered signal e(n) that is obtained after applying the inventive filtering technique to the pressure signal d(n). The filtered signal e(n) is made up of second pulses and noise. It should be noted that there is an absence of second pulses after about 4 seconds, which may be observed by the surveillance device (25 in FIG. 1) and identified as a fault condition of the fluid containing system.

Figure 2:
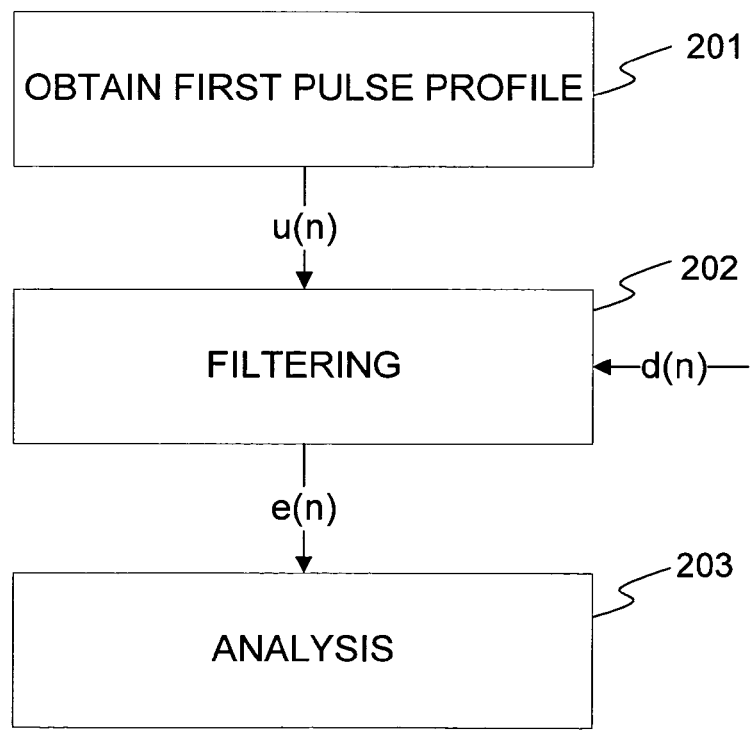
FIG. 2 is a flow chart of a monitoring process according to an embodiment of the invention.

Reverting to FIG. 2, the inventive data processing comprises two main steps: a determination of the first pulse profile u(n) (step 201) and a removal of one or more first pulses from a measurement signal d(n) using the first pulse profile u(n) (step 202).

There are many ways to implement these main steps. For example, the first pulse profile (standard signal profile) may be obtained in a reference measurement, based on a measurement signal from one or more of the pressure sensors 4*a*-4*c* in the first sub-system S1, suitably by identifying and possibly averaging a set of first pulse segments in the measurement signal(s). The first pulse profile may or may not be updated intermittently during the actual monitoring of the aforesaid functional state or parameter. Alternatively, a predetermined (i.e. predefined) standard signal profile may be used, which optionally may be modified according to a mathematical model accounting for wear in the first pulse generator, fluid flow rates, tubing dimensions, speed of sound in the fluid, etc. Further, the removal may involve subtracting the first pulse profile from the measurement signal at suitable amplitude and phase. The phase may be indicated by phase information which may be obtained from a signal generated by a phase sensor coupled to the first pulse generator 3, or from a control signal for the first pulse generator 3.

The inventive filtering may also be combined with other filtering techniques to further improve the quality of the filtered signal e(n). In one embodiment, the filtered signal e(n) could be passed through a bandpass filter with a passband in the relevant frequency range for the second pulses. If the second pulses originate from a human heart, the passband may be located within the approximate range of 0.5-4 Hz, corresponding to heart pulse rates of 30-240 beats per minute. In another embodiment, if the current frequency range (or ranges) of the second pulses is known, the passband of the bandpass filter could be actively controlled to a narrow range around the current frequency range. For example, such an active control may be applied whenever the rates of first and second pulses are found to differ by more than a certain limit, e.g. about 10%. The current frequency range may be obtained from the pressure signal, either by intermittently shutting off the first pulse generator 3, or intermittently preventing the first pulses from reaching the relevant pressure sensor 4*a*-4*c*. Alternatively, the current frequency range may be obtained from a dedicated sensor in either the first or the second sub-systems S1, S2, or based on a control unit (not shown) for the second pulse generator 3'. According to yet another alternative, the location and/or width of the passband could be set, at least in part, based on patient-specific information, i.e. existing data records for the patient, e.g. obtained in earlier treatments of the same patient. The patient-specific information may be stored in an internal memory of the surveillance device (25 in FIG. 1), on an external memory which is made accessible to the surveillance device, or on a patient card where the information is e.g. transmitted wirelessly to the surveillance device, e.g. by RFID (Radio Frequency IDentification).

These and other embodiments will be explained in further detail below, within the context of a system for extracorporeal blood treatment. To facilitate the following discussion, details of an exemplifying extracorporeal blood flow circuit will be first described.

Monitoring in an Extracorporeal Blood Flow Circuit

Figure 4:
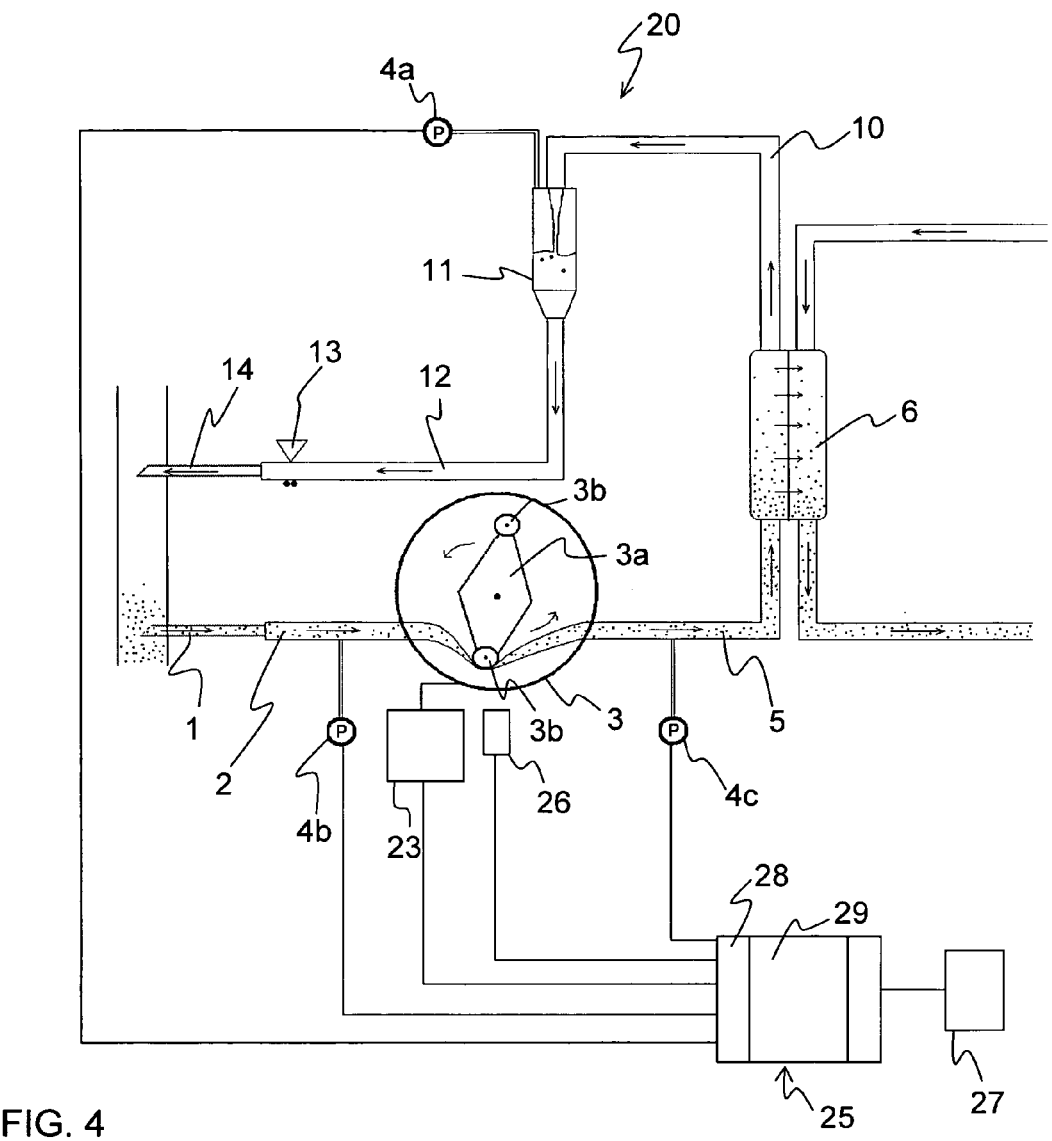
FIG. 4 is a schematic view of a system for hemodialysis treatment including an extracorporeal blood flow circuit.

FIG. 4 shows an example of an extracorporeal blood flow circuit 20 of the type which is used for dialysis. The extracorporeal blood flow circuit 20 (also denoted "extracorporeal circuit") comprises components 1-14 to be described in the following. Thus, the extracorporeal circuit 20 comprises an access device for blood extraction in the form of an arterial needle 1, and an arterial tube segment 2 which connects the arterial needle 1 to a blood pump 3 which may be of peristaltic type, as indicated in FIG. 4. At the inlet of the pump there is a pressure sensor 4b (hereafter referred to as "arterial sensor") which measures the pressure before the pump in the arterial tube segment 2. The blood pump 3 forces the blood, via a tube segment 5, to the blood-side of a dialyser 6. Many dialysis machines are additionally provided with a pressure sensor 4c (hereafter referred to as "system sensor") that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4a (hereafter referred to as "venous sensor") is provided to measure the pressure on the venous side of the dialyser 6. In the illustrated example, the pressure sensor 4a measures the pressure in the venous drip chamber. Both the arterial needle 1 and the venous needle 14 are connected to the patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters. The access devices 1, 14 may alternatively be combined into a single unit.

In relation to the fluid containing system in FIG. 1, the extracorporeal circuit 20 corresponds to the first sub-system S1, the blood pump 3 (as well as any further pulse source(s) within or associated with the extracorporeal circuit 20, such as a dialysis solution pump, valves, etc) corresponds to the first pulse generator 3, the blood system of the patient corresponds to the second sub-system S2, and the fluid connection C corresponds to at least one of the venous-side and arterial-side fluid connections between the patient and the extracorporeal circuit 20.

In FIG. 4, a control unit 23 is provided, i.a., to control the blood flow in the extracorporeal circuit 20 by controlling the revolution speed of the blood pump 3. The extracorporeal circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

The system in FIG. 4 also includes a surveillance/monitoring device 25, which is connected to receive a pressure signal from at least one of the pressure sensors 4a-4c and which executes the inventive data processing. In the example of FIG. 4, the surveillance device 25 is also connected to the control unit 23. Alternatively or additionally, the device 25 may be connected to a pump sensor 26 for indicating the revolution speed and/or phase of the blood pump 3. It is to be understood that the surveillance device 25 may include inputs for further data, e.g. any other system parameters that represent the overall system state (see e.g. discussion with reference to FIG. 7 below). The device 25 is tethered or wirelessly connected to a local or remote device 27 for generating an audible/visual/tactile alarm or warning signal. Alternatively or additionally, either device 25, 27 may include a display or monitor for displaying the functional state or parameter resulting from the analysis step (203 in FIG. 2), and/or the filtered signal e(n) resulting from the filtering step (202 in FIG. 2), e.g. for visual inspection.

In FIG. 4, the surveillance device 25 comprises a data acquisition part 28 for pre-processing the incoming signal(s), e.g. including an A/D converter with a required minimum sampling rate and resolution, one or more signal amplifiers, and one or more filters to remove undesired components of the incoming signal(s), such as offset, high frequency noise and supply voltage disturbances.

Figure 5:
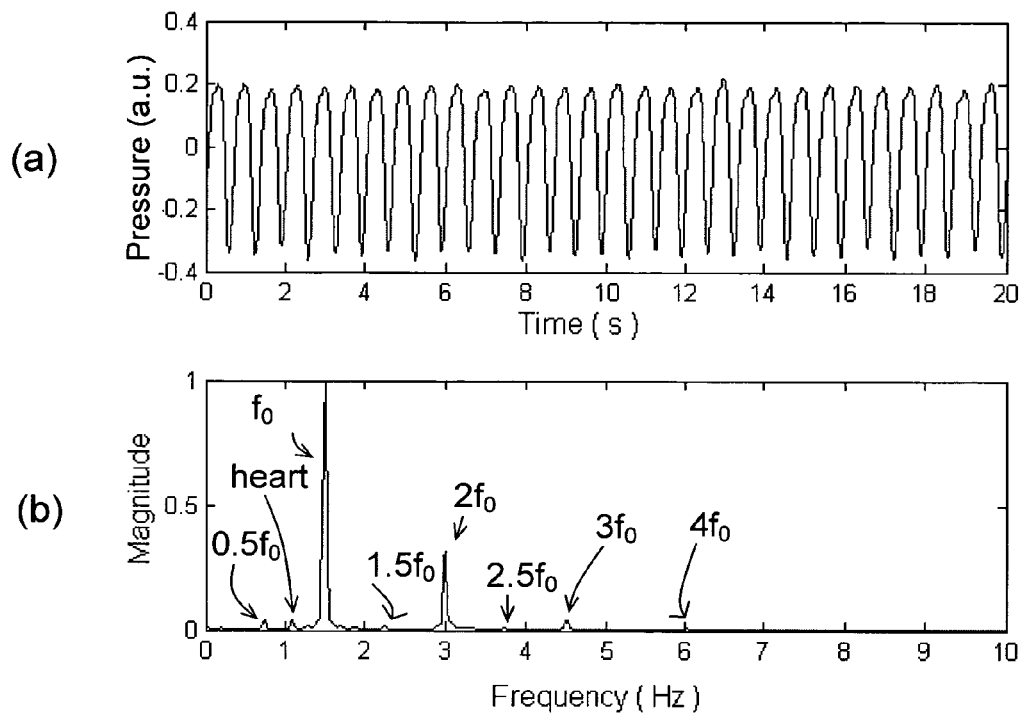
FIG. 5(a) is a plot in the time domain of a venous pressure signal containing both pump frequency components and a heart signal.
FIG. 5(b) is a plot of the corresponding signal in the frequency domain.

After the pre-processing in the data acquisition part 28, the pre-processed pressure signal is provided as input to a main data processing part 29, which executes the inventive data processing. FIG. 5(a) shows an example of such a pre-processed pressure signal in the time domain, and FIG. 5(b) shows the corresponding power spectrum, i.e. the pre-processed pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pump frequency in the following, is the frequency of the pump strokes that generate pressure waves in the extracorporeal circuit 20. For example, in a peristaltic pump of the type shown in FIG. 4, two pump strokes are generated for each full revolution of the rotor 3a. FIG. 5(b) also indicates the presence of a frequency component at half the pump frequency ($0.5f_0$) and harmonics thereof, in this example at least $f_0$, $1.5f_0$, $2f_0$ and $2.5f_0$. FIG. 5(b) also shows a heart signal (at 1.1 Hz) which in this example is approximately 40 times weaker than the blood pump signal at the base frequency $f_0$.

The main data processing part 29 executes the aforesaid steps 201-203. In step 202, the main data processing part 29 operates to filter the pre-processed pressure signal in the time domain, and outputs a filtered signal or monitoring signal (e(n) in FIG. 2) in which the signal components of the blood pump 3 have been removed. The monitoring signal still contains any signal components that originate from the patient (cf. FIG. 3(b)), such as pressure pulses caused by the beating of the patient's heart. There are a number of sources to cyclic physiological phenomena that may generate pressure pulses in the blood stream of the patient, including the heart, the breathing system, or the vasomotor, which is controlled by the autonomic nervous system. Thus, the monitoring signal may contain pressure pulses resulting from a combination of cyclic phenomena in the patient. Generally speaking, the signal components in the monitoring signal may originate from any type of physiological phenomenon in the patient, or combinations thereof, be it cyclic or non-cyclic, repetitive or non-repetitive, autonomous or non-autonomous.

Depending on implementation, the surveillance device 25 may be configured apply further filtering to the monitoring signal to isolate signal components originating from a single cyclic phenomenon in the patient. Alternatively, such signal component filtering is done during the pre-processing of the pressure signal (by the data acquisition part 28). The signal component filtering may be done in the frequency domain, e.g. by applying a cut-off or bandpass filter, since the signal components of the different cyclic phenomena in the patient are typically separated in the frequency domain. Generally, the heart frequency is about 0.5-4 Hz, the breathing frequency is about 0.15-0.4 Hz, the frequency of the autonomous system for regulation of blood pressure is about 0.04-0.14 Hz, the frequency of the autonomous system for regulation of body temperature is about 0.04 Hz.

The surveillance device 25 could be configured to monitor the breathing pattern of the patient, by identifying breathing pulses in the monitoring signal. The resulting information could be used for on-line surveillance for apnoea, hyperventilation, hypoventilation, asthmatic attacks or other irregular breathing behaviours of the patient. The resulting information could also be used to identify coughing, sneezing, vomiting or seizures. The vibrations resulting from coughing/sneezing/vomiting/seizures might disturb other measurement or surveillance equipment that is connected to the patient or the extracorporeal circuit 20. The surveillance device 25 may be arranged to output information about the timing of any coughing/sneezing/vomiting/seizures, such that other measurement or surveillance equipment can take adequate measures to reduce the likelihood that the coughing/sneezing/vomiting/seizures results in erroneous measurements or false alarms. Of course, the ability of identifying coughing/sneezing/vomiting/seizures may also have a medical interest of its own.

The surveillance device 25 could be configured to monitor the heart rate of the patient, by identifying heart pulses in the monitoring signal.

The surveillance device 25 could be configured to collect and store data on the time evolution of the heart rate, the breathing pattern, etc, e.g. for subsequent trending or statistical analysis.

The surveillance device 25 may be configured to monitor the integrity of the fluid connection between the patient and the extracorporeal circuit 20, in particular the venous-side fluid connection (via access device 14). This could be done by monitoring the presence of a signal component originating from, e.g., the patient's heart or breathing system in the monitoring signal. Absence of such a signal component may be taken as an indication of a failure in the integrity of the fluid connection C, and could bring the device 25 to activate an alarm and/or stop the blood flow, e.g. by stopping the blood pump 3 and activating a clamping device 13 on the tube segment 12. For monitoring the integrity of the venous-side fluid connection, also known as VNM (Venous Needle Monitoring), the surveillance device 25 may be configured to generate the monitoring signal based on a pressure signal from the venous sensor 4a. The device 25 may also be connected to pressure sensors 4b, 4c, as well as any additional pressure sensors included in the extracorporeal circuit 20.

The extracorporeal circuit 20 may have the option to operate in a hemodiafiltration mode (HDF mode), in which the control unit 23 activates a second pumping device (HDF pump, not shown) to supply an infusion solution into the blood line upstream and/or downstream of the dialyser 6, e.g. into one or more of tube segments 2, 5, 10 or 12.

Obtaining the Predicted Signal Profile of First Pulses

This section describes different embodiments for predicting or estimating the signal profile of first pulses in the system shown in FIG. 4. The predicted signal profile is typically given as a series of pressure values over a period of time normally corresponding to at least one complete pump cycle of the blood pump 3.

Figure 6:
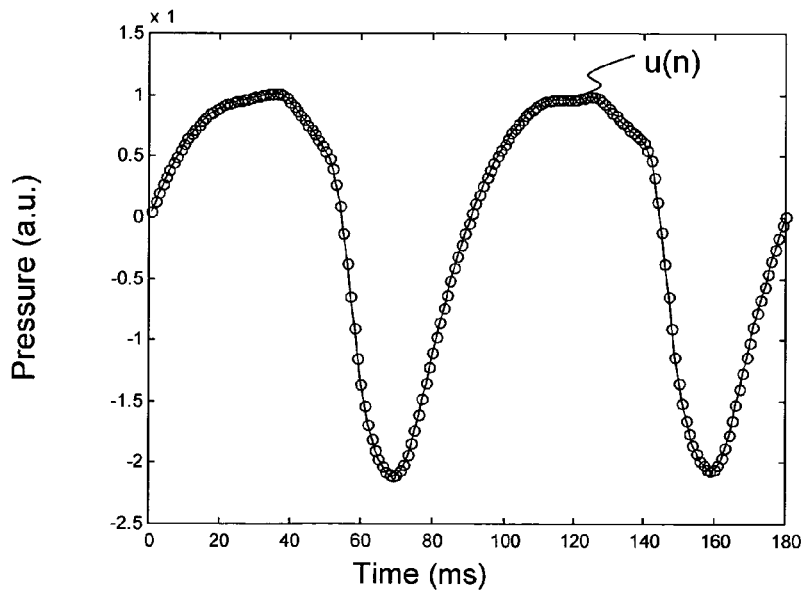
FIG. 6 is a plot of a predicted signal profile originating from a peristaltic pump in the system of FIG. 4.

FIG. 6 illustrates an example of a predicted signal profile for the system in FIG. 4. Since the blood pump 3 is a peristaltic pump, in which two rollers 3b engage a tube segment during a full revolution of the rotor 3a, the pressure profile consists of two pump strokes. The pump strokes may result in different pressure values (pressure profiles), e.g. due to slight differences in the engagement between the rollers 3b and the tube segment, and thus it may be desirable for the predicted signal profile to represent both pump strokes. If a lower accuracy of the predicted signal profile can be tolerated, i.e. if the output of the subsequent removal process is acceptable, the predicted signal profile might represent one pump stroke only.

On a general level, the predicted signal profile may be obtained in a reference measurement, through mathematical simulation of the fluid system, or combinations thereof.

Reference Measurement

A first main group of methods for obtaining the predicted signal profile is based on deriving a time-dependent reference pressure signal ("reference signal") from a pressure sensor in the system, typically (but not necessarily) from the same pressure sensor that provides the measurement signal (pressure signal) that is to be processed for removal of first pulses. During this reference measurement, the second pulses are prevented from reaching the relevant pressure sensor, either by shutting down/deactivating the second pulse generator 3' or by isolating the pressure sensor from the second pulses. In the system of FIG. 4, the reference measurement could be carried out during a priming phase, in which the extracorporeal circuit 20 is detached from the patient and a priming fluid is pumped through the blood lines. Alternatively, the reference measurement could be carried in a simulated treatment with blood or any other fluid. Optionally, the reference measurement could involve averaging a plurality of pressure profiles to reduce noise. For example, a plurality of relevant signal segments may be identified in the reference signal, whereupon these segments are aligned to achieve a proper overlap of the pressure profiles in the different segments and then added together. The identifying of relevant signal segments may be at least partially based on timing information which indicates the expected position of each first pulse in the reference signal. The timing information may be obtained from a trigger point in the output signal of the pump sensor 26, in a control signal of the control unit 23, or in the pressure signal from another one of the pressure sensors 4a-4c. For example, a predicted time point of a first pulse in the reference signal can be calculated based on a known difference in arrival time between the trigger point and the pressure sensor that generates the reference signal. In variant, if the reference signal is periodic, relevant signal segments may be identified by identifying crossing points of the reference signal with a given signal level, wherein the relevant signal segments are identified to extend between any respective pairs of crossing points.

In a first embodiment, the predicted signal profile is directly obtained in a reference measurement before the extracorporeal circuit 20 is connected to the patient, and is then used as input to the subsequent removal process, which is executed when the extracorporeal circuit 20 is connected to the patient. In this embodiment, it is thus assumed that the predicted signal profile is representative of the first pulses when the system is connected to the patient. Suitably, the same pump frequency/speed is used during the reference measurement and during the removal process. It is also desirable that other relevant system parameters are maintained essentially constant.

Figure 7:
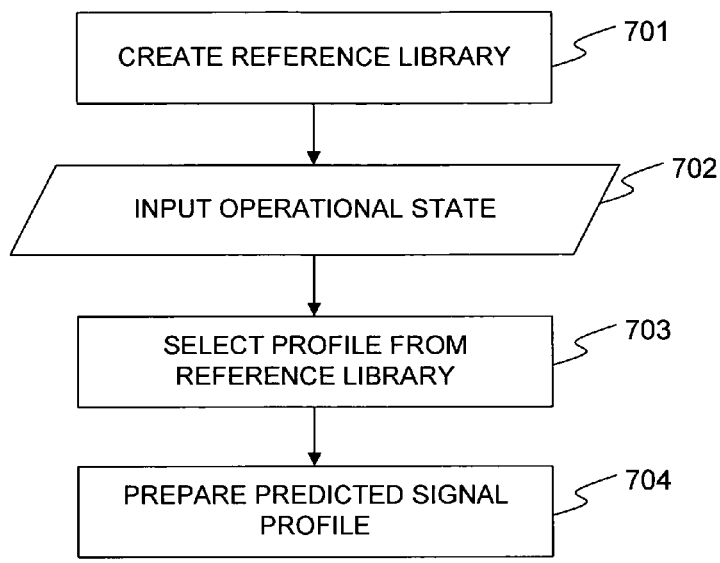
FIG. 7 is a flow chart of a process for obtaining the predicted signal profile.

FIG. 7 is a flow chart of a second embodiment. In the second embodiment, a reference library or database is first created based on the reference measurement (step 701). The resulting reference library is typically stored in a memory unit, e.g. RAM, ROM, EPROM, HDD, Flash, etc (cf. 25b in FIG. 1) of the surveillance device (cf. 25 in FIG. 1). During the reference measurement, reference pressure signals are acquired for a number of different operational states of the extracorporeal circuit. Each operational state is represented by a unique combination of system parameter values. For each operational state, a reference profile is generated to represent the signal profile of the first pulses. The reference profiles together with associated system parameter values are then stored in the reference library, which is implemented as a searchable data structure, such as a list, look-up table, search tree, etc.

During the actual monitoring process, i.e. when first pulses are to be eliminated from the measurement signal, current state information indicating the current operational state of the fluid containing system is obtained from the system, e.g. from a sensor, a control unit or otherwise (step 702). The current state information may include a current value of one or more system parameters. The current value is then matched against the system parameter values in the reference library. Based on the matching, one or more reference profiles are selected (step 703) and used for preparing the predicted signal profile (step 704).

Generally, the aforesaid system parameters represent the overall system state, including but not limited to the structure, settings, status and variables of the fluid containing system or its components. In the system of FIG. 4, exemplary system parameters may include:

Pump-related parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc Dialysis machine settings: temperature, ultrafiltration rate, mode changes, valve position/changes, etc Disposable dialysis equipment/material: information on pump chamber/pump segment (material, geometry and wear status), type of blood line (material and geometry), type of dialyser, type and geometry of access devices, etc Dialysis system variables: actual absolute pressures of the system upstream and downstream of the blood pump, e.g. venous pressure (from sensor 4a), arterial pressure (from sensor 4b) and system pressure (from sensor 4c), gas volumes trapped in the flow path, blood line suspension, fluid type (e.g. blood or dialysis fluid), etc Patient status: blood access properties, blood properties such as e.g. hematocrit, plasma protein concentration, etc It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the fluid containing system during the monitoring process. In other words, the pump frequency is used as search variable in the reference library. The pump frequency may e.g. be given by a set value for the blood flow rate output from the control unit, or by an output signal of a sensor that indicates the frequency of the pump (cf. pump sensor 26 in FIG. 4). Alternatively, the pump frequency could be obtained by frequency analysis of the pressure signal from any of the sensors 4a-4c during operation of the fluid system. Such frequency analysis could be achieved by applying any form of harmonics analysis to the pressure signal, such as Fourier or wavelet analysis. As indicated in FIG. 5(b), the base frequency $f_0$ of the pump can be identified in a resulting power spectrum.

Figure 8:
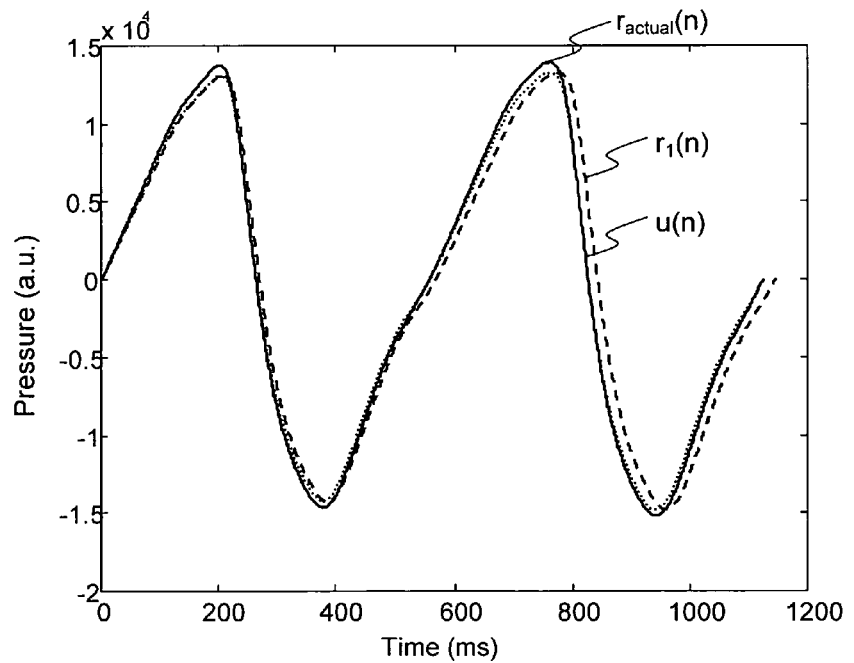
FIG. 8 is a plot to illustrate an extrapolation process for generating the predicted signal profile.

In a first example, the reference library is searched for retrieval of the reference profile that is associated with the pump frequency that lies closest to the current pump frequency. If no exact match is found to the current pump frequency, an extrapolation process is executed to generate the predicted signal profile. In the extrapolation process, the retrieved reference profile is scaled in time to the current pump cycle, based on the known difference ("pump frequency difference") between the current pump frequency and the pump frequency associated with the retrieved reference profile. The amplitude scale may also be adjusted to compensate for amplitude changes due to pump frequency, e.g. based on a known function of amplitude as a function of pump frequency. FIG. 8 illustrates a reference profile $r_1(n)$ obtained at a flow rate of 470 ml/min, and predicted signal profile u(n) which is obtained by scaling the reference profile to a flow rate of 480 ml/min. For comparison only, a reference profile $r_{actual}(n)$ obtained at 480 ml/min is also shown, to illustrate that extrapolation process indeed may yield a properly predicted signal profile.

In a second example, the reference library is again searched based on current pump frequency. If no exact match is found to the current pump frequency, a combination process is executed to generate the predicted signal profile. Here, the reference profiles associated with the two closest matching pump frequencies are retrieved and combined. The combination may be done by re-scaling the pump cycle time of the retrieved reference profiles to the current pump frequency and by calculating the predicted signal profile via interpolation of the re-scaled reference profiles. For example, the predicted signal profile u(n) at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved reference profiles, obtained at a pump frequency $v_i$ and $v_j$, respectively, after re-scaling to the current pump frequency v, and g is a relaxation parameter which is given as a function of the frequency difference $(v-v_i)$, wherein $v_i \le v \le v_j$ and $0 \le g \le 1$. The skilled person realizes that the predicted signal profile u(n) may be generated by combining more than two reference profiles.

Figure 9A:
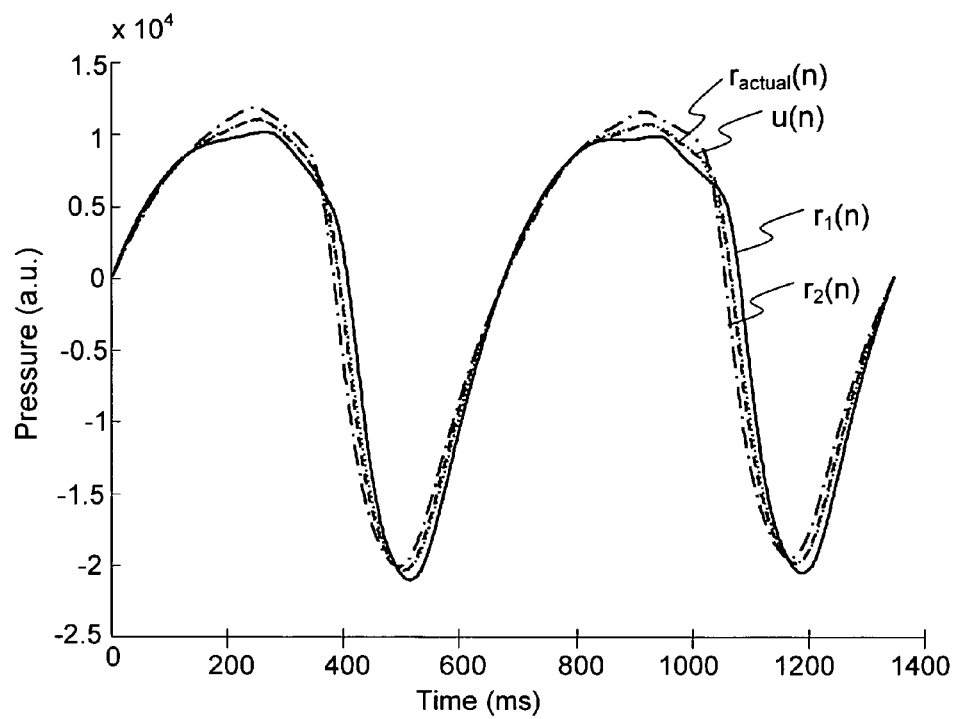
FIG. 9(a) is a plot to illustrate an interpolation process for generating the predicted signal profile.
Figure 9B:
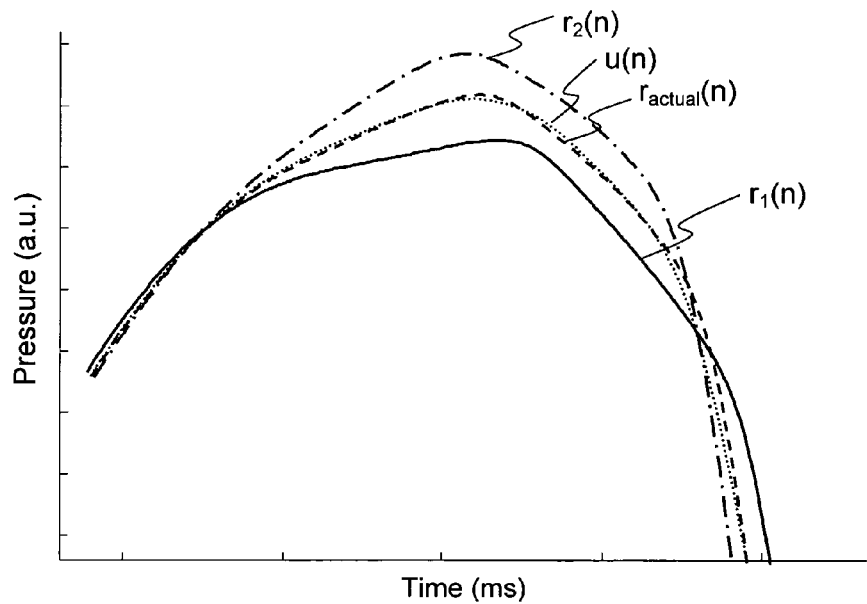
FIG. 9(b) is an enlarged view of FIG. 9(a).

FIG. 9(a) illustrates a predicted signal profile u(n) at a current flow rate of 320 ml/min for a measurement signal obtained from the venous sensor 4a in the system of FIG. 4. The predicted signal profile u(n) has been calculated as an average of a reference profile $r_1(n)$ obtained at a flow rate of 300 ml/min from the venous sensor and a reference profile $r_2(n)$ obtained at a flow rate of 340 ml/min from the venous sensor. For comparison only, a reference profile $r_{actual}(n)$ obtained at 320 ml/min is also shown, to illustrate that the combination process indeed may yield a properly predicted signal profile. In fact, the differences are so small that they are only barely visible in the enlarged view of FIG. 9(b).

The first and second examples may be combined, e.g. by executing the extrapolation process of the first example if the pump frequency difference is less than a certain limit, and otherwise executing the combination process of the second example.

In a third embodiment, like in the second embodiment shown in FIG. 7, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data are then stored in a reference library together with the associated system parameter values (cf. step 701 in FIG. 7). The implementation of the reference library may be the same as in the second embodiment.

During the actual monitoring process, i.e. when first pulses are to be eliminated from the measurement signal, a current value of one or more system parameters is obtained from the fluid containing system (cf. step 702 in FIG. 7). The current value is then matched against the system parameter values in the reference library. Based on the matching, a specific set of energy and phase data may be retrieved from the reference library to be used for generating the predicted signal profile (cf. step 703 in FIG. 7). Generally, the predicted signal profile is generated by adding sinusoids of appropriate frequency, amplitude and phase, according to the retrieved energy and phase data (cf. step 704 in FIG. 7).

Generally speaking, without limiting the present disclosure, it may be advantageous to generate the predicted signal profile from energy and phase data when the first pulses (to be removed) contain only one or a few base frequencies (and harmonics thereof), since the predicted signal profile can be represented by a small data set (containing energy and phase data for the base frequencies and the harmonics). One the other hand, when the power spectrum of the first pulses is more complex, e.g. a mixture of many base frequencies, it may instead be preferable to generate the predicted signal profile from one or more reference profiles.

FIG. 10(*a*) represents an energy spectrum of a reference signal acquired at a flow rate of 300 ml/min in the system of FIG. 4. In this example, the reference signal essentially consists of a basic pump frequency at 1.2 Hz ($f_0$, first harmonic) and a set of overtones of this frequency (second and further harmonics). Compared to the power spectrum of FIG. 5(*b*), the pressure signals used for generating the graphs in FIG. 10(*a*)-10(*d*) do not contain any significant frequency component at $0.5f_0$ and its harmonics. The graph in FIG. 10(*a*) displays the relative energy distribution, wherein the energy values have been normalized to the total energy for frequencies in the range of 0-10 Hz. FIG. 10(*b*) represents energy spectra of reference signals acquired at three different flow rates in the system of FIG. 4. The energy spectra are given in logarithmic scale versus harmonic number (first, second, etc). As shown, an approximate linear relationship can be identified between the logarithmic energy and harmonic number for the first four to five harmonic numbers. This indicates that each energy spectrum may be represented by a respective exponential function. FIG. 10(*c*) illustrates the data of FIG. 10(*b*) in linear scale, wherein a respective polynomial function has been fitted to the data. As indicated in FIGS. 10(*a*)-10(*c*), the energy spectra may be represented in different formats in the reference library, e.g. as a set of energy values associated with discrete frequency values or harmonic numbers, or as an energy function representing energy versus frequency/harmonic number.

FIG. 10(*d*) illustrates a phase angle spectrum acquired together with the energy spectrum in FIG. 10(*a*), i.e. for a flow rate of 300 ml/min. The graph in FIG. 10(*d*) illustrates phase angle as a function of frequency, and a linear function has been fitted to the data. In an alternative representation (not shown), the phase spectrum may be given as a function of harmonic number. Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library can be used to generate the predicted signal profile. Each energy value in the energy data corresponds to an amplitude of a sinusoid with a given frequency (the frequency associated with the energy value), wherein the phase value for the given frequency indicates the proper phase angle of the sinousoid. This method of preparing the predicted signal profile by combining (typically adding) sinusoids of appropriate frequency, amplitude and phase angle allows the predicted signal profile to include all harmonics of the pump frequency within a desired frequency range.

When a predicted signal profile is to be generated, the reference library is first searched based on a current value of one or more system parameters, such as the current pump frequency. If no exact match is found in the reference library, a combination process may be executed to generate the predicted signal profile. For example, the two closest matching pump frequencies may be identified in the reference library and the associated energy and phase data may be retrieved and combined to form the predicted signal profile. The combination may be done by interpolating the energy data and the phase data. In the example of FIGS. 10(*a*)-10(*d*), an interpolated energy value may be calculated for each harmonic number, and similarly an interpolated phase value could be calculated for each harmonic number. Any type of interpolation function could be used, be it linear or non-linear.

In the first, second and third embodiments, the reference signals and the measurement signals are suitably obtained from the same pressure sensor unit in the fluid containing system. Alternatively, different pressure sensor units could be used, provided that the pressure sensor units yield identical signal responses with respect to the first pulses or that the signal responses can be matched using a known mathematical relationship.

To further improve the first, second and third embodiments, the process of generating the predicted signal profile may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or look-up tables.

Figure 10A:
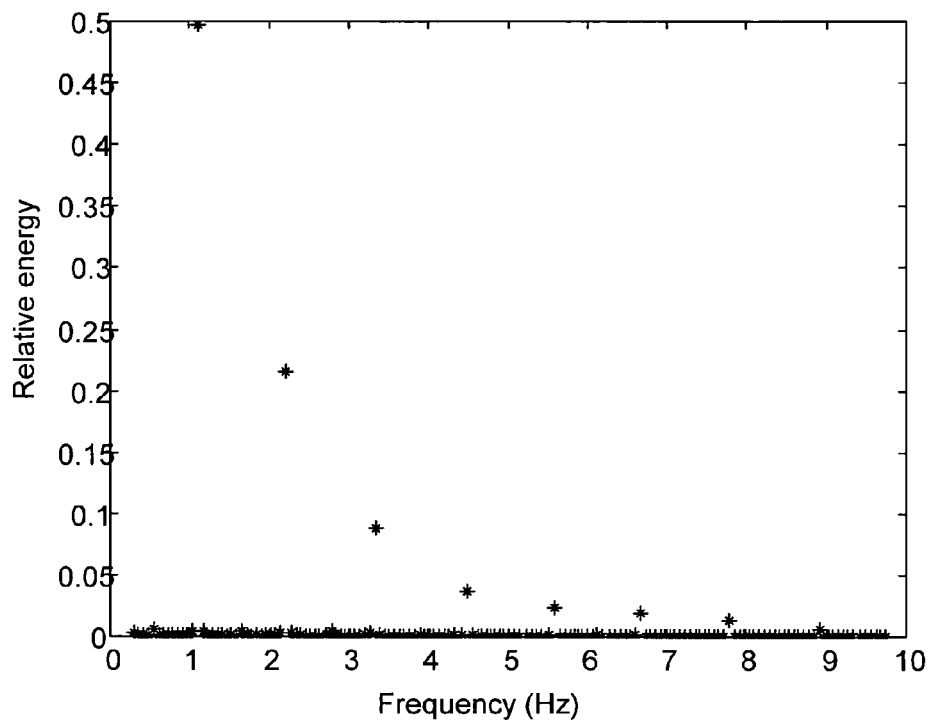
FIG. 10(a) represents a frequency spectrum of a pressure pulse originating from a pumping device at one flow rate.
Figure 10B:
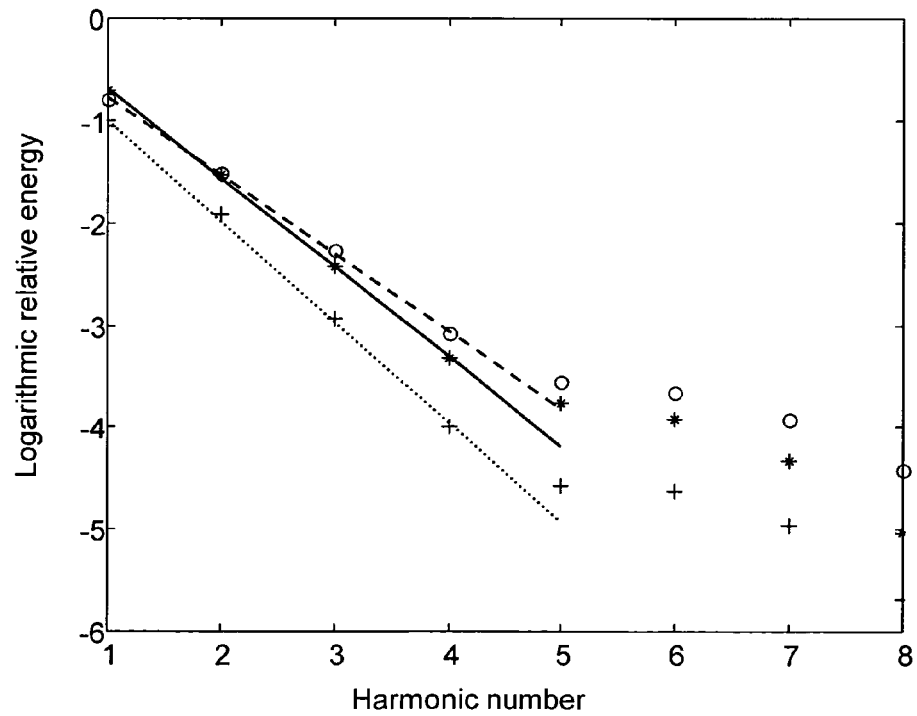
FIG. 10(b) represents corresponding frequency spectra for three different flow rates, wherein each frequency spectrum is given in logarithmic scale and mapped to harmonic numbers.
Figure 10C:
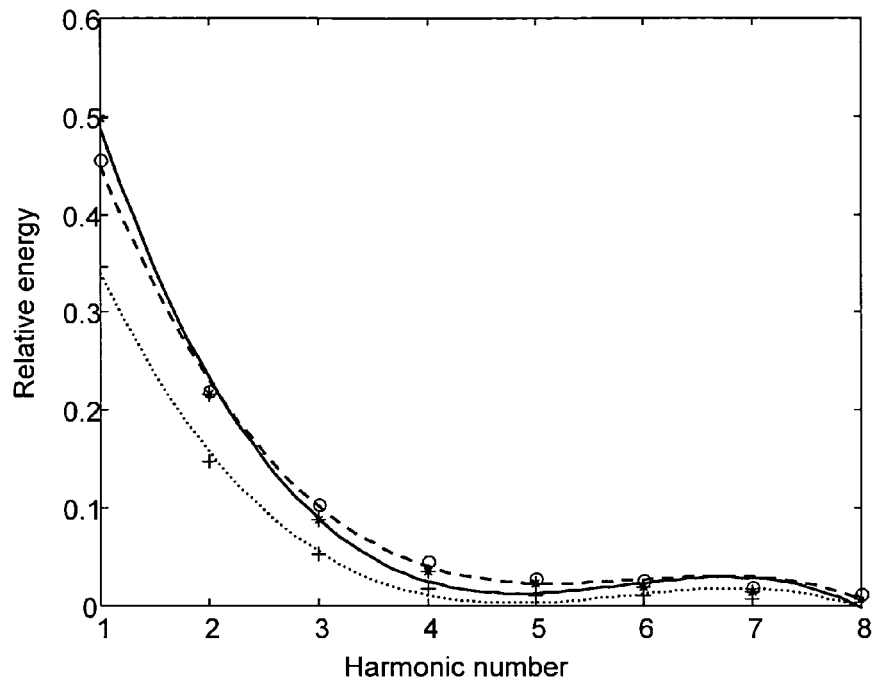
FIG. 10(c) is a plot of the data in FIG. 10(b) in linear scale.
Figure 10D:
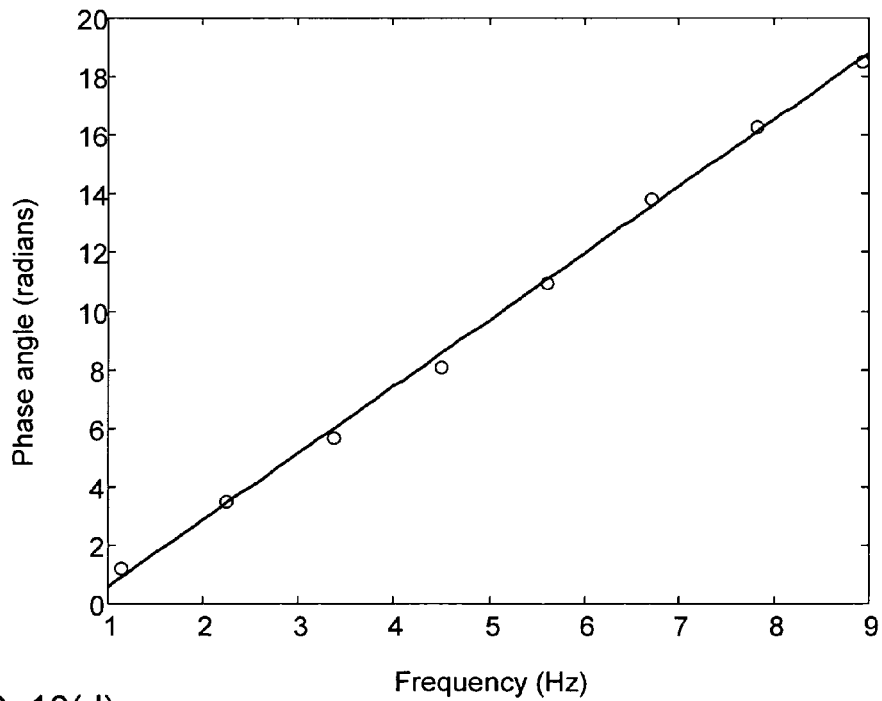
FIG. 10(d) is a phase angle spectrum corresponding to the frequency spectrum in FIG. 10(a).

In further variations, the second and third embodiments may be combined, e.g. in that the reference library stores not only energy and phase data, but also reference profiles, in association with system parameter value(s). When an exact match is found in the library, the reference profile is retrieved from the library and used as the predicted signal profile, otherwise the predicted signal profile is obtained by retrieving and combining (e.g. interpolating) the energy and phase data, as in the third embodiment. In a variant, the predicted signal profile u(n) at the current pump frequency v is obtained by:

$$u(n)=r_i(n)-r^r_i(n)+r^r(n),$$

wherein $r_i(n)$ denotes a reference profile that is associated with the closest matching pump frequency $v_i$ in the reference library, $r^r_i(n)$ denotes a reference profile that is reconstructed from the energy and phase data associated with the closest matching pump frequency $v_i$ in the reference library, and $r^r(n)$ denotes an estimated reference profile at the current pump frequency v. The estimated reference profile $r'(n)$ may be obtained by applying predetermined functions to estimate the energy and phase data, respectively, at the current pump frequency v based on the energy and phase data associated with the closest matching pump frequency $v_i$. With reference to FIGS. 10(b)-10(c), such a predetermined function may thus represent the change in energy data between different flow rates. Alternatively, the estimated reference profile $r'(n)$ may be obtained by retrieving and combining (e.g. interpolating) energy and phase data for the two closest matching pump frequencies $v_i$ and $v_j$ as in the third embodiment.

In a further variant, the reference measurement is made during regular operation of the fluid containing system, instead of or in addition to any reference measurements made before regular operation (e.g. during priming or simulated treatments with blood). Such a variant presumes that it is possible to intermittently shut off the second pulse generator, or to intermittently prevent the second pulses from reaching the relevant pressure sensor. This approach is more difficult in the extracorporeal circuit 20 of FIG. 4 if the reference signals and the measurement signals are obtained from the one and the same pressure sensor. However, this approach can e.g. be applied if the fluid system includes one pressure sensor that is substantially isolated from the second pulses. In such a situation, the reference profile (or reference spectra) may be obtained from the isolated sensor, and used for generating the predicted signal profile (optionally after adjustment/modification for differences in confounding factors), which is then used for removing first pulses from a measurement signal that contains both first and second pulses. For example, the pressure signal from the system sensor 4c in the circuit 20 of FIG. 4 may be essentially isolated from the second pulses that originate from the patient, and this pressure signal may thus be used in a reference measurement.

As explained above, the extracorporeal circuit 20 in FIG. 4 may be switched into a HDF mode, in which an additional HDF pump is activated to supply an infusion liquid into the blood line of the extracorporeal circuit 20. Such a change of operating mode may cause a change in the signal characteristics of the first pulses in the measurement signal. Thus, it may necessary to account for this change, by ensuring that the reference library includes appropriate reference data (reference profiles and/or energy and phase angle data) associated with this operational state.

Alternatively, it may be desirable to isolate the pressure pulses originating from the HDF pump. This could be achieved by obtaining a reference profile from the pressure signal of the arterial sensor 4b (FIG. 4). The arterial pressure signal includes pressure pulses originating from the patient and from the blood pump 3, whereas pressure pulses originating from the HDF pump are significantly damped by the patient and the blood pump 3, respectively, and thus barely reach the arterial sensor 4b. On the other hand, the pressure signals of the venous sensor 4a and the system sensor 4c contain pressure pulses originating from both the patient, the blood pump 3 and the HDF pump. Thus, the arterial pressure signal may be used for obtaining the predicted signal profile of the combined pressure pulses originating from the blood pump 3 and the patient as they should look in the pressure signal from the venous sensor 4a or the system sensor 4c. The predicted signal profile may then be used for isolating the pressure pulses originating from the HDF pump in the pressure signal from the venous sensor 4a or the system sensor 4c. In this example, the patient and the extracorporeal circuit 20 could be regarded as a first sub-system (S1 in FIG. 1) and the HDF pump and the associated infusion tubing could be regarded as a second sub-system (S2 in FIG. 1), which are connected via a fluid connection. Thus, in this example, the inventive data processing is not applied to isolate pulses originating from a cyclic physiological phenomenon in the patient, but pulses originating from another pump in the fluid system. It should be realized that in other arrangements, the reference profile may be obtained from the pressure signal of the venous sensor 4a (FIG. 4), and used for processing the pressure signal of the arterial sensor 4b or system sensor 4c.

Simulations

As an alternative to the use of reference measurements, the predicted signal profile may be obtained directly through simulations, i.e. calculations using a mathematical model of the fluid containing system, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model could be anything from a complete physical description of the system to a simple function. In one example, such a simple function could convert data on the instantaneous angular velocity of the pump rotor 3a to a predicted signal profile, using empirical or theoretical data. Such data on the instantaneous angular velocity might be obtained from the pump sensor 26 in FIG. 4.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

Removal of First Pulses

There are several different ways of removing one or more first pulses from the measurement signal, using the predicted signal profile. Here, two different removal processes will be described: Single Subtraction and Adaptive Filtering. Of course, the description of removal processes and their implementations is not comprehensive (neither of the different alternatives nor of the implementations), which is obvious to a person skilled in the art.

Depending on implementation, the predicted signal profile may be input to the removal process as is, or the predicted signal profile may be duplicated to construct an input signal of suitable length for the removal process.

Single Subtraction

In this removal process, a single predicted signal profile is subtracted from the measurement signal. The predicted signal profile may be shifted and scaled in time and scaled in amplitude in any way, e.g. to minimize the error of the removal. Different minimization criterions may be used for such an auto-scaling, e.g., minimizing the sum of the squared errors, or the sum of the absolute errors. Alternatively or additionally, the predicted signal profile is shifted in time based on timing information that indicates the expected timing of the first pulse(s) in the measurement signal. The timing information may be obtained in the same way as described above in relation to the averaging of pressure segments in the reference signal.

One potential limitation of this removal process is that the relationship between different frequencies in the predicted signal profile is always the same, since the process only shifts and scales the predicted signal profile. Thus, it is not possible to change the relationship between different harmonic frequencies, neither is it possible to use only some of the frequency content in the predicted signal profile and to suppress other frequencies. To overcome this limitation, adaptive filtering may be used since it uses a linear filter before subtraction, e.g. as described in the following.

Adaptive Filtering

Figure 11:
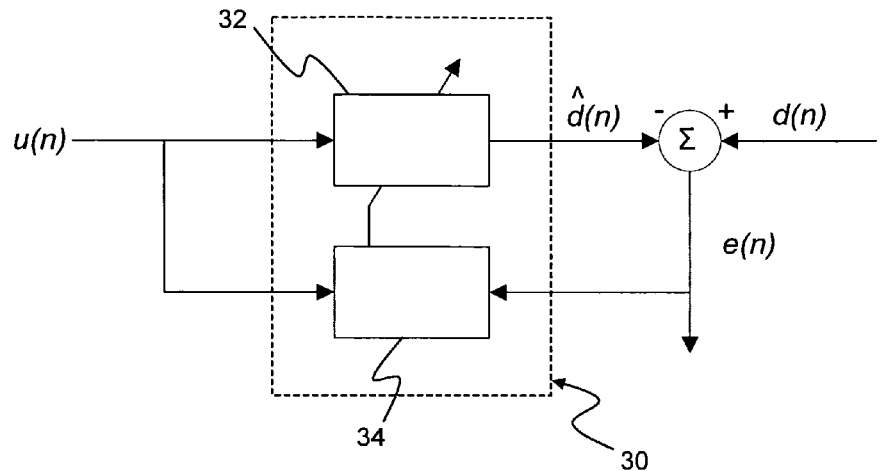
FIG. 11 is schematic view of an adaptive filter structure operable to filter a measurement signal based on a predicted signal profile.

FIG. 11 is a schematic overview of an adaptive filter 30 and an adaptive filter structure which is designed to receive the predicted signal profile u(n) and a measurement signal d(n), and to output an error signal e(n) which forms the aforesaid monitoring signal in which the first pulses are removed.

Adaptive filters are well-known electronic filters (digital or analog) that self-adjust their transfer function according to an optimizing algorithm. Specifically, the adaptive filter 30 includes a variable filter 32, typically a finite impulse response (FIR) filter of length M with filter coefficients w(n).

Even if adaptive filters are known in the art, they are not readily applicable to cancel the first pulses in the measurement signal d(n). In the illustrated embodiment, this has been achieved by inputting the predicted signal profile u(n) to the variable filter 32, which processes the predicted signal profile u(n) to generate an estimated measurement signal $\hat{d}(n)$, and to an adaptive update algorithm 34, which calculates the filter coefficients of the variable filter 32 based on the predicted signal profile u(n) and the error signal e(n). The error signal e(n) is given by the difference between the measurement signal d(n) and the estimated measurement signal $\hat{d}(n)$.

Basically, the adaptive filtering also involves a subtraction of the predicted signal profile u(n) from the measurement signal d(n), since each of the filter coefficients operates to shift and possibly re-scale the amplitude of the predicted signal profile u(n). The estimated measurement signal $\hat{d}(n)$, which is subtracted from the measurement signal d(n) to generate the error signal e(n), is thus formed as a linear combination of M shifted predicted signal profiles u(n), i.e. a linear filtering of u(n).

The adaptive update algorithm 34 may be implemented in many different ways, some of which will be described below. The disclosure is in no way limited to these examples, and the skilled person should have no difficulty of finding further alternatives based on the following description.

There are two main approaches to adaptive filtering: stochastic and deterministic. The difference lies in the minimization of the error signal e(n) by the update algorithm 34, where different minimization criteria are obtained whether e(n) is assumed to be stochastic or deterministic. A stochastic approach typically uses a cost function J with an expectation in the minimization criterion, while a deterministic approach typically uses a mean. The squared error signal $e^2(n)$ is typically used in a cost function when minimizing e(n), since this results in one global minimum. In some situations, the absolute error |e(n)| may be used in the minimization, as well as different forms of constrained minimizations. Of course, any form of the error signal may be used, however convergence towards a global minimum is not always guaranteed and the minimization may not always be solvable.

In a stochastic description of the signal, the cost function may typically be according to, $J(n)=E\{|e(n)|^2\}$, and in a deterministic description of the signal the cost function may typically be according to, $J(n)=\Sigma e^2(n)$.

The first pulses will be removed from the measurement signal d(n) when the error signal e(n) (cost function J(n)) is minimized. Thus, the error signal e(n) will be cleaned from first pulses while retaining the second pulses, once the adaptive filter 30 has converged and reached the minimum error.

In order to obtain the optimal filter coefficients w(n) for the variable filter 32, the cost function J needs to be minimized with respect to the filter coefficients w(n). This may be achieved with the cost function gradient vector $\nabla J$, which is the derivative of J with respect to the different filter coefficients $w_0, w_1, \ldots, w_{M-1}$. Steepest Descent is a recursive method (not an adaptive filter) for obtaining the optimal filter coefficients that minimize the cost function J. The recursive method is started by giving the filter coefficients an initial value, which is often set to zero, i.e., w(0)=0. The filter coefficients is then updated according to, $$w(n+1) = w(n) + \frac{1}{2}\mu[-\nabla J(n)],$$

where w is given by, $w=[w_0 w_1 \ldots w_{M-1}]^T M \times 1$.

Furthermore, the gradient vector $\nabla J$ points in the direction in which the cost is growing the fastest. Thus, the filter coefficients are corrected in the direction opposite to the gradient, where the length of the correction is influenced through the step size parameter $\mu$. There is always a risk for the Steepest Descent algorithm to diverge, since the algorithm contains a feedback. This sets boundaries on the step size parameter $\mu$ in order to ensure convergence. It may be shown that the stability criterion for the Steepest Descent algorithm is given by, $$0 < \mu < \frac{2}{\lambda_{max}}$$

where $\lambda_{max}$ is the largest eigenvalue of R, the correlation matrix of the predicted signal profile u(n), given by $$R = E[\bar{u}(n)\bar{u}^T(n)] = \begin{bmatrix} r(0) & r(1) & \ldots & r(M-1) \\ r(1) & r(0) & & r(M-2) \\ \vdots & \vdots & \ddots & \vdots \\ r(M-1) & r(M-2) & \ldots & r(0) \end{bmatrix},$$

where $\bar{u}(n)$ is given by, $\bar{u}(n)=[u(n)u(n-1)\ldots u(n-M+1)]^T M \times 1$.

If the mean squared error (MSE) cost function (defined by $J=E\{|e(n)|^2\}$) is used, it may be shown that the filter coefficients are updated according to, $w(n+1)=w(n)+\mu E[\bar{u}(n)e(n)]$, where e(n) is given by, $e(n)=d(n)-\bar{u}^T(n)w(n)$.

The Steepest Descent algorithm is a recursive algorithm for calculation of the optimal filter coefficients when the statistics of the signals are known. However, this information is often unknown. The Least Mean Squares (LMS) algorithm is a method that is based on the same principles as the Steepest Descent algorithm, but where the statistics is estimated continuously. Thus, the LMS algorithm is an adaptive filter, since the algorithm can adapt to changes in the signal statistics (due to continuous statistic estimations), although the gradient may become noisy. Because of the noise in the gradient, the LMS algorithm is unlikely to reach the minimum error $J_{min}$, which the Steepest Descent algorithm does. Instantaneous estimates of the expectation are used in the LMS algorithm, i.e., the expectation is removed. Thus, for the LMS algorithm, the update equation of the filter coefficients becomes $$w(n+1)=w(n)+\mu \overline{u}(n)e(n).$$

The convergence criterion of the LMS algorithm is the same as for the Steepest Descent algorithm. In the LMS algorithm, the step size is proportional to the predicted signal profile u(n), i.e., the gradient noise is amplified when the predicted signal profile is strong. One solution to this problem is to normalize the update of the filter coefficients with $$\|\overline{u}(n)\|^2 = \overline{u}^T(n)u(n).$$

The new update equation of the filter coefficients is called the Normalized LMS, and is given by $$w(n+1) = w(n) + \frac{\tilde{\mu}}{a + \|\overline{u}(n)\|^2}\overline{u}(n)e(n),$$

where $0<\tilde{\mu}<2$, and a is a positive protection constant.

There are many more different alternatives to the LMS algorithm, where the step size is modified. One of them is to use a variable adaptation step, $$w(n+1)=w(n)+\alpha(n)\overline{u}(n)e(n),$$

where $\alpha(n)$ for example may be, $$\alpha(n) = \frac{1}{n+c},$$

where c is a positive constant. It is also possible to choose independent adaptation steps for each filter coefficient in the LMS algorithm, e.g., according to, $$w(n+1)=w(n)+A\overline{u}(n)e(n),$$

where A is given by, $$A = \begin{bmatrix} \alpha_1 & 0 & 0 & \cdots & 0 \\ 0 & \alpha_2 & 0 & \cdots & 0 \\ 0 & 0 & \alpha_3 & \cdots & 0 \\ \vdots & \vdots & \vdots & \ddots & \vdots \\ 0 & 0 & 0 & \cdots & \alpha_M \end{bmatrix}.$$

If instead the following cost function $$J(n)=E\{|e(n)|\}$$

is used, then the update equation becomes $$w(n+1)=w(n)+\alpha \text{sign}[e(n)]\overline{u}(n).$$

This adaptive filter is called the Sign LMS, which is used in applications with extremely high requirements on low computational complexity.

Another adaptive filter is the Leaky LMS, which uses a constrained minimization with the following cost function $$J(n)=E\{|e(n)|^2\}+\alpha\|w(n)\|^2.$$

This constraint has the same effect as if white noise with variance $\alpha$ was added to the predicted signal profile u(n). As a result, the uncertainty in the input signal u(n) is increased, which tends to hold the filter coefficients back. The Leaky LMS is preferably used when R, the correlation matrix of u(n), has one or more eigenvalues equal to zero. However, in systems without noise, the Leaky LMS makes performance poorer. The update equation of the filter coefficients for the Leaky LMS is given by, $$w(n+1)=(1-\mu\alpha)w(n)+\mu\overline{u}(n)e(n).$$

Instead of minimizing the MSE cost function as above, the Recursive Least Squares (RLS) adaptive filter algorithm minimizes the following cost function $$J(n) = \sum_{i=1}^{n} \lambda^{n-i}|e(i)|^2,$$

where $\lambda$ is called forgetting factor, $0<\lambda \leq 1$, and the method is called Exponentially Weighted Least Squares. It may be shown that the update equations of the filter coefficients for the RLS algorithm are, after the following initialization $$w(0)=0_{M\times 1}$$

$$P(0)=\delta^{-1}I_{M\times M}$$

where $I_{M\times M}$ is the identity matrix M×M, given according to $$k(n) = \frac{\lambda^{-1}P(n-1)\overline{u}(n)}{1+\lambda^{-1}\overline{u}^T(n)P(n-1)\overline{u}(n)}$$

$$\xi(n)=d(n)-w^T(n-1)\overline{u}(n)$$

$$w(n)=w(n-1)+k(n)\xi(n)$$

$$P(n)=\lambda^{-1}P(n-1)-\lambda^{-1}k(n)\overline{u}^T(n)P(n-1),$$

where $\delta$ is a small positive constant for high signal-to-noise ratio (SNR), and a large positive constant for low SNR, $\delta<<0.01\sigma_u^2$, and $\xi(n)$ corresponds to e(n) in the preceding algorithms. During the initialization phase the following cost function $$J(n) = \sum_{i=1}^{n} \lambda^{n-i}|e(i)|^2 + \delta\lambda^n\|w(n)\|^2,$$

is minimized instead, due to the use of the initialization $P(0)=\delta^{-1}$ I. The RLS algorithm converges in approximately 2M iterations, which is considerably faster than for the LMS algorithm. Another advantage is that the convergence of the RLS algorithm is independent of the eigenvalues of R, which is not the case for the LMS algorithm.

Several RLS algorithms running in parallel may be used with different $\lambda$ and $\delta$, which may be combined in order to improve performance, i.e., $\lambda=1$ may also be used in the algorithm (steady state solution) with many different $\delta$:s.

It should be noted that both the LMS algorithm and the RLS algorithm can be implemented in fixed-point arithmetic, such that they can be run on a processor that has no floating point unit, such as a low-cost embedded microprocessor or microcontroller.

Figure 12A:
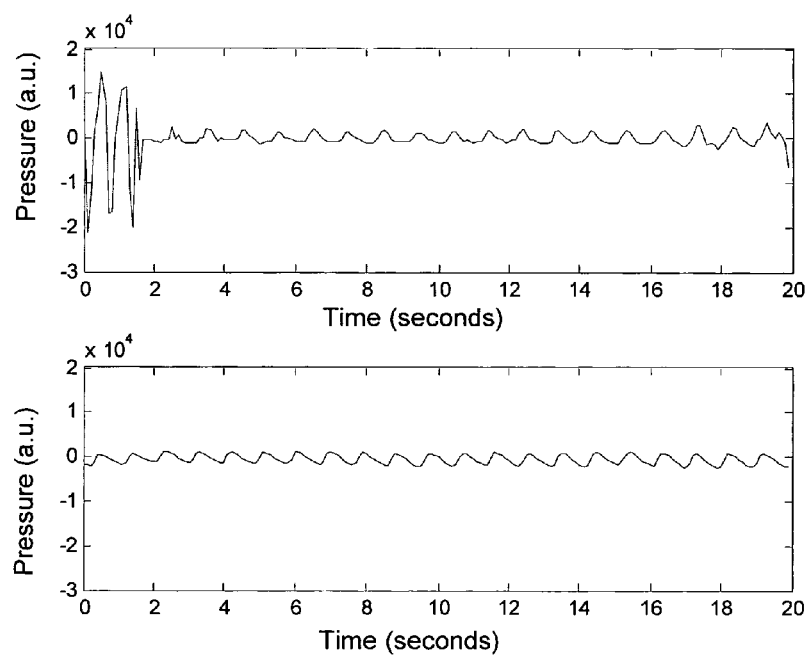
FIG. 12(a) illustrates a filtered pressure signal (top) and a corresponding heart signal (bottom), obtained from a venous pressure sensor.

To illustrate the effectiveness of the removal process using an adaptive filter, the top graph in FIG. 12($a$) illustrates the error signal e(n) output by the adaptive filter structure in FIG. 11, using an RLS algorithm as adaptive update algorithm 32, operating on a measurement signal from the venous sensor 4$a$ in FIG. 4, at a flow rate of 430 ml/min. The adaptive filter structure is provided with a predicted signal profile obtained in a reference measurement at the same flow rate. The RLS algorithm, designed with M=15, converges after about 2M, which equals 3 seconds with the current sampling frequency of 10 Hz. The top graph thus shows the measurement signal after elimination of the first pulses. The bottom graph in FIG. 12(a) is included for reference, and shows the measurement signal from the venous sensor 4a while the blood pump 3 is stopped. Clearly, the adaptive filtering is operable to provide, after a convergence period, a monitoring signal that properly represents the second pulses.

Figure 12B:
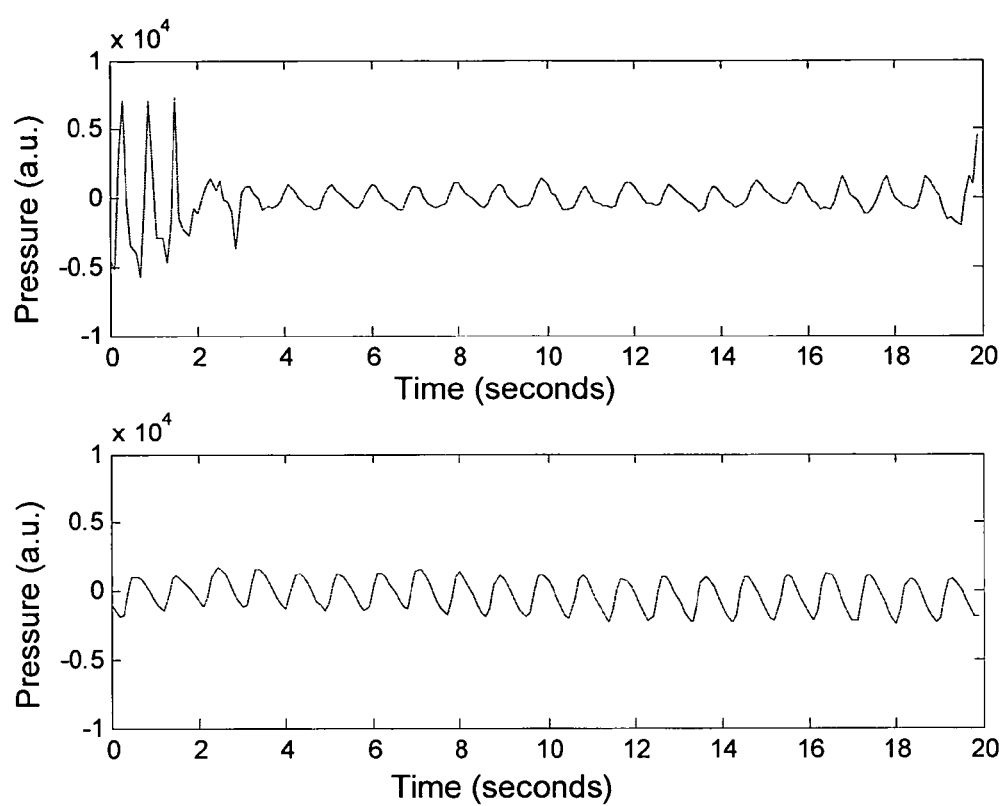
FIG. 12(b) illustrates a filtered pressure signal (top) and a corresponding heart signal (bottom), obtained from an arterial pressure sensor.

FIG. 12(b) corresponds to FIG. 12(a), but is obtained for a measurement signal from the arterial sensor 4b in FIG. 4.

Irrespective of implementation, the performance of the adaptive filter 30 (FIG. 11) may be further improved by switching the adaptive filter 30 to a static mode, in which the update algorithm 34 is disabled and thus the filter coefficients of the filter 32 (FIG. 11) are locked to a current set of values. The switching of the adaptive filter 30 may be controlled by an external process that analyses the second pulses in the error signal e(n), typically in relation to first pulse data. The first pulse data may be obtained from the measurement signal, a reference signal (see above), a dedicated pulse sensor, a control unit for the first pulse generator, etc. The adaptive filter 30 may be switched into the static mode if the external process reveals that the rate of second pulses starts to approach the rate of the first pulses and/or that the amplitude of the second pulses is very weak (in relation to an absolute limit, or in relation to a limit given by the amplitude of the first pulses). The adaptive filter may remain in static mode for a predetermined time period, or until released by the process.

The invention has mainly been described above with reference to a few embodiments. However, as is readily appreciated by a person skilled in the art, other embodiments than the ones disclosed above are equally possible within the scope and spirit of the invention.

For example, the measurement and reference signals may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, accelerometers, etc.

Although FIG. 1 indicates that the pressure sensor 4a-4c is connected to the first sub-system S1, it may instead be connected to measure the fluid pressure in the second sub-system S2. Further, the fluid containing system need not be partitioned into first and second sub-systems S1, S2 connected via a fluid connection C, but could instead be a unitary fluid containing system associated with a first pulse generator and a second pulse generator, wherein the each pressure sensor is arranged in the fluid containing system to detect a first pulse originating from the first pulse generator and a second pulse originating from the second pulse generator.

Further, the inventive technique is applicable for monitoring in all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for monitoring in other types of extracorporeal blood flow circuits, such as circuits for blood transfusion, infusion, as well as heart-lung-machines.

The inventive technique is also applicable to fluid systems containing other liquids than blood.

Further, the inventive technique is applicable to remove pressure pulses originating from any type of pumping device, not only rotary peristaltic pumps as disclosed above, but also other types of positive displacement pumps, such as linear peristaltic pumps, diaphragm pumps, as well as centrifugal pumps. In fact, the inventive technique is applicable for removing pressure pulses that originate from any type of pulse generator, be it mechanic or human.

Likewise, the inventive technique is applicable to isolate pressure pulses originating from any type of pulse generator, be it human or mechanic.

The inventive technique need not operate on real-time data, but could be used for processing off-line data, such as a previously recorded measurement signal.

The invention claimed is:

1. A method for processing a time-dependent measurement signal obtained from a pressure sensor in a fluid containing system associated with a first pulse generator and a second pulse generator, wherein the pressure sensor is arranged in the fluid containing system to detect a first pulse originating from the first pulse generator and a second pulse originating from the second pulse generator, wherein the fluid containing system comprises an extracorporeal blood flow circuit for connection to a blood system in a human body, and wherein the first pulse generator comprises a pumping device in the extracorporeal blood flow circuit, and wherein the second pulse generator comprises a physiological pulse generator in the human body, said method comprising:
receiving the time-dependent measurement signal,
obtaining a first pulse profile which is a predicted temporal signal profile of the first pulse, and
filtering the time-dependent measurement signal in the time-domain to output an error signal in which the first pulse is essentially eliminated while the second pulse is retained, wherein said filtering comprises: supplying the measurement signal and the first pulse profile as input to an adaptive filter structure comprising an adaptive filter; calculating the error signal between the measurement signal and an output signal of the adaptive filter; and providing the error signal as input to the adaptive filter, whereby the adaptive filter is arranged to essentially eliminate the first pulse in the error signal.

2. The method of claim 1, wherein the first pulse profile is obtained in a reference measurement in said fluid containing system, wherein the reference measurement comprises: operating the first pulse generator to generate at least one first pulse, and obtaining the first pulse profile from a reference signal generated by a reference pressure sensor in the fluid containing system.

3. The method of claim 2, wherein the first pulse generator is operated to generate a sequence of first pulses during the reference measurement, and wherein the first pulse profile is obtained by identifying and averaging a set of first pulse segments in the reference signal.

4. The method of claim 2, wherein the reference measurement is effected intermittently during operation of the fluid containing system to provide an updated first pulse profile.

5. The method of claim 2, wherein the pressure sensor is used as said reference pressure sensor.

6. The method of claim 2, wherein the fluid containing system is operated, during the reference measurement, such that the reference signal contains a first pulse and no second pulse.

7. The method of claim 2, wherein the reference measurement comprises: obtaining a combined pulse profile based on a first reference signal containing a first pulse and a second pulse; obtaining a second pulse profile based on a second reference signal containing a second pulse and no first pulse, and obtaining the predicted signal profile by subtracting the second pulse profile from the combined pulse profile.

8. The method of claim 1, wherein said obtaining comprises obtaining a predetermined signal profile.

9. The method of claim 8, wherein said obtaining further comprises modifying the predetermined signal profile according to a mathematical model based on a current value of one or more system parameters of the fluid containing system.

10. The method of claim 1, further comprising obtaining a current value of one or more system parameters of the fluid containing system, wherein the first pulse profile is obtained as a function of the current value.

11. The method of claim 10, wherein obtaining the first pulse profile as a function of the current value comprises: identifying, based on the current value, one or more reference profiles in a reference database; and obtaining the first pulse profile based on said one or more reference profiles.

12. The method of claim 11, wherein said one or more system parameters is indicative of the rate of first pulses in the fluid containing system.

13. The method of claim 12, wherein the first pulse generator comprises a pumping device and the system parameter is indicative of a pump frequency of the pumping device.

14. The method of claim 11, wherein each reference profile in the reference database is obtained by a reference measurement in the fluid containing system for a respective value of said one or more system parameters.

15. The method of claim 10, wherein said obtaining the first pulse profile as a function of the current value comprises: identifying, based on the current value, one or more combinations of energy and phase angle data in a reference database, and obtaining the first pulse profile based on said one or more combinations of energy and phase angle data.

16. The method of claim 15, wherein the first pulse profile is obtained by combining a set of sinusoids of different frequencies, wherein the amplitude and phase angle of each sinusoid is given by said one or more combinations of energy and phase angle data.

17. The method of claim 10, wherein said obtaining the first pulse profile as a function of the current value comprises: inputting the current value into an algorithm which calculates the response of the pressure sensor based on a mathematical model of the fluid containing system.

18. The method of claim 1, wherein the adaptive filter comprises a finite impulse response filter with filter coefficients that operate on the first pulse profile to generate the output signal, and an adaptive algorithm which optimizes the filter coefficients as a function of the error signal and the first pulse profile.

19. The method of claim 18, wherein the output signal is formed as a linear combination of M shifted first pulse profiles, wherein M is the length of the finite impulse response filter.

20. The method of claim 19, wherein at least one of the M shifted first pulse profiles being linearly combined is re-scaled in amplitude.

21. The method of claim 1, further comprising controlling the adaptive filter to lock the filter coefficients, based on a comparison of the rate, the amplitude, or the rate and amplitude of the second pulses to a limit value.

22. The method of claim 1, wherein the second pulse generator is at least one of a heart, a breathing system, and a vasomotor affected by an autonomic nervous system.

23. The method of claim 1, wherein the extracorporeal blood flow circuit comprises an arterial access device, a blood processing device, and a venous access device, wherein the human blood system comprises a blood vessel access, wherein the arterial access device is configured to be connected to the human blood system, wherein the venous access device is configured to be connected to the blood vessel access to form a fluid connection, and wherein the first pulse generator comprises a pumping device arranged in the extracorporeal blood flow circuit to pump blood from the arterial access device through the blood processing device to the venous access device, said method further comprising receiving the measurement signal either from a venous pressure sensor located downstream of the pumping device, or from an arterial pressure sensor located upstream of the pumping device.

* * * * *

UNITED STATES PATENT AND TRADEMARK OFFICE
CERTIFICATE OF CORRECTION

PATENT NO. : 8,715,216 B2  Page 1 of 1
APPLICATION NO. : 13/000856
DATED : May 6, 2014
INVENTOR(S) : Olde et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 557 days.

Signed and Sealed this
Twenty-ninth Day of September, 2015

Michelle K. Lee
*Director of the United States Patent and Trademark Office*